US011988671B2

(12) United States Patent
Blyn et al.

(10) Patent No.: US 11,988,671 B2
(45) Date of Patent: May 21, 2024

(54) ASSAYS FOR DETECTING SARS-COV-2

(71) Applicant: Abbott Rapid Diagnostics International Unlimited Company, Dublin (IE)

(72) Inventors: Lawrence B. Blyn, Abbott Park, IL (US); Mijung Ji, Seoul (KR); Stephen Kovacs, Abbott Park, IL (US); Anthony S. Muerhoff, Abbott Park, IL (US); Stacey P. Huth, Scarborough, ME (US); Carsten Buenning, Gross-Rohrheim (DE); Tao Xin, Carlsbad, CA (US); Donabel Roberts, Carlsbad, CA (US); Sung Hee Kim, Gyeonggi-do (KR); Sang Yong Park, Gyeonggi-do (KR); Robert N. Ziemann, Abbott Park, IL (US)

(73) Assignee: Abbott Rapid Diagnostics International Unlimited Company, Dublin (IE)

( * ) Notice: Subject to any disclaimer, the term of this patent is extended or adjusted under 35 U.S.C. 154(b) by 203 days.

(21) Appl. No.: 17/394,058

(22) Filed: Aug. 4, 2021

(65) Prior Publication Data
US 2022/0043003 A1 Feb. 10, 2022

Related U.S. Application Data

(60) Provisional application No. 63/126,336, filed on Dec. 16, 2020, provisional application No. 63/067,051, filed on Aug. 18, 2020, provisional application No. 63/065,898, filed on Aug. 14, 2020, provisional application No. 63/060,975, filed on Aug. 4, 2020.

(51) Int. Cl.
*G01N 33/68* (2006.01)
*G01N 33/543* (2006.01)

(52) U.S. Cl.
CPC ... *G01N 33/6857* (2013.01); *G01N 33/54388* (2021.08); *G01N 33/6893* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 4,828,981 A | 5/1989 | Maggio et al. | |
| 5,034,506 A | 7/1991 | Summerton et al. | |
| 5,063,081 A | 11/1991 | Cozzette et al. | |
| 5,225,539 A | 7/1993 | Winter | |
| 5,468,646 A | 11/1995 | Mattingly et al. | |
| 5,480,792 A | 1/1996 | Buechler et al. | |
| 5,525,524 A | 6/1996 | Buechler et al. | |
| 5,530,101 A | 6/1996 | Queen et al. | |
| 5,543,524 A | 8/1996 | Mattingly et al. | |
| 5,545,739 A | 8/1996 | Mattingly et al. |
| 5,565,570 A | 10/1996 | Mattingly et al. |
| 5,585,089 A | 12/1996 | Queen et al. |
| 5,620,850 A | 4/1997 | Bamdad et al. |
| 5,622,871 A | 4/1997 | May et al. |
| 5,669,819 A | 9/1997 | Mattingly et al. |
| 5,679,526 A | 10/1997 | Buechler et al. |
| 5,693,762 A | 12/1997 | Queen et al. |
| 5,714,352 A | 2/1998 | Jakobovits |
| 5,723,323 A | 3/1998 | Kauffman et al. |
| 5,763,192 A | 6/1998 | Kauffman et al. |
| 5,766,886 A | 6/1998 | Studnicka et al. |
| 5,770,429 A | 6/1998 | Lonberg et al. |
| 5,783,699 A | 7/1998 | Mattingly et al. |
| 5,814,476 A | 9/1998 | Kauffman et al. |
| 5,817,483 A | 10/1998 | Kauffman et al. |
| 5,824,514 A | 10/1998 | Kauffman et al. |
| 5,824,799 A | 10/1998 | Buechler et al. |
| 5,833,985 A | 11/1998 | Ball et al. |
| 5,837,243 A | 11/1998 | Deo et al. |
| 5,851,776 A | 12/1998 | Valkirs |
| 5,885,527 A | 3/1999 | Buechler |
| 5,922,615 A | 7/1999 | Nowakowski et al. |
| 5,922,845 A | 7/1999 | Deo et al. |
| 5,939,272 A | 8/1999 | Buechler et al. |

(Continued)

FOREIGN PATENT DOCUMENTS

EP 3183271 A1 6/2017
EP 3543259 A2 9/2019

(Continued)

OTHER PUBLICATIONS

Kussie PH, Parhami-Seren B, Wysocki LJ, Margoies MN (1994), "A Single Engineered Aimno Acid Substitution Changes Antibody Fine Specificity", Journal of Immunology 152, 1, pp. 146-152 (Year: 1994).*
Vasudevan S, Celikel R, Ruggeri ZM, Varghese KI, Kunicki TJ (2004), "A single amino acid change in the binding pocket alters specificity of an anti-integrin antibody AP7.4 as revealed by its crystal structure", Blood Cells, Molecules, and Diseases, 32, pp. 176-181 (Year: 2004).*
Wei Z, Feng J, Lin HY, Mullapudi S, Bishop E, Tous GI, Casas-Finet J, Hakki F, Strouse R, Schener. (2007), "Identification of a Single Tryptophan Residue as Critical for Binding Activity in a Humanized Monoclonal Antibody against Respiratory Syncytial Virus" , Analytical Chemistry, 79, pp. 2797-2805 (Year: 2007).*

(Continued)

*Primary Examiner* — Ellen J Marcsisin
*Assistant Examiner* — Stefanie J. Kirwin
(74) *Attorney, Agent, or Firm* — Casimir Jones, S.C.; Kelly A. Barton; Thomas A. Isenbarger

(57) ABSTRACT

The present disclosure relates to methods of detecting a protein from the SARS-CoV-2 virus, or a fragment thereof, in a sample obtained from a subject using a first antibody or antigen-binding fragment thereof that binds to a protein from the SARS-CoV-2 virus, or a fragment thereof, and a second antibody or antigen-binding fragment thereof which binds to a protein from the SARS-CoV-2 virus, or a fragment thereof.

15 Claims, 1 Drawing Sheet
Specification includes a Sequence Listing.

(56) References Cited

U.S. PATENT DOCUMENTS

| | | | |
|---|---|---|---|
| 5,947,124 | A | 9/1999 | Buechler et al. |
| 5,976,862 | A | 11/1999 | Kauffman et al. |
| 5,985,579 | A | 11/1999 | Buechler et al. |
| 6,017,517 | A | 1/2000 | Park |
| 6,019,944 | A | 2/2000 | Buechler et al. |
| 6,096,311 | A | 8/2000 | Fanger et al. |
| 6,111,166 | A | 8/2000 | Van De |
| 6,113,855 | A | 9/2000 | Buechler |
| 6,143,576 | A | 11/2000 | Buechler |
| 6,180,370 | B1 | 1/2001 | Queen et al. |
| 6,187,598 | B1 | 2/2001 | May et al. |
| 6,204,023 | B1 | 3/2001 | Robinson et al. |
| 6,270,765 | B1 | 8/2001 | Deo et al. |
| 6,365,116 | B1 | 4/2002 | Barham et al. |
| 6,410,690 | B1 | 6/2002 | Deo et al. |
| 6,485,982 | B1 | 11/2002 | Charlton |
| 6,565,808 | B2 | 5/2003 | Hudak et al. |
| 6,682,928 | B2 | 1/2004 | Keler et al. |
| 6,809,687 | B2 | 10/2004 | Yuanzhu |
| 6,984,720 | B1 | 1/2006 | Korman et al. |
| 7,419,821 | B2 | 9/2008 | Davis et al. |
| 7,682,833 | B2 | 3/2010 | Miller et al. |
| 7,723,099 | B2 | 5/2010 | Miller et al. |
| 8,568,992 | B2 | 10/2013 | Walker et al. |
| 8,828,739 | B2 | 9/2014 | Guo et al. |
| 10,717,082 | B2 | 7/2020 | Tran |
| 11,022,598 | B2 | 6/2021 | Huff et al. |
| 2004/0018577 | A1 | 1/2004 | Emerson Campbell et al. |
| 2006/0134713 | A1 | 6/2006 | Rylatt et al. |
| 2017/0342161 | A1 | 11/2017 | Moon et al. |

FOREIGN PATENT DOCUMENTS

| | | |
|---|---|---|
| WO | WO 2001/058956 | 8/2001 |
| WO | WO 2005/010034 A1 | 2/2005 |
| WO | WO 2006/073748 A2 | 7/2006 |
| WO | WO 2009/110918 A1 | 9/2009 |
| WO | WO 2009/128963 A2 | 10/2009 |
| WO | WO 2011/102563 | 8/2011 |
| WO | WO 2016/161400 | 10/2016 |
| WO | WO 2018/088878 A2 | 5/2018 |
| WO | WO 2020/114399 A1 | 6/2020 |

OTHER PUBLICATIONS

Ohno S, Mori N, Matsunaga T (1985), "Antigen-binding specificities of antibodies are primarily determined by seven residues of VH", PNAS, 82, pp. 2945-2949. (Year: 1985).*

Grant BD, Anerson CE, Williford JR, Alonzo LF, Glukhova VA, et al. (Jul. 1, 2020) "SARS-CoV-2 Coronavirus Nucleocapsid Antigen-Detecting Half-Strip Lateral Flow Assay Toward the Development of Point of Care Tests Using Commercially Available Reagents", Analytical Chemistry, 92, 16, pp. 11305-11309. (Year: 2020).*

Adamczyk, M. et al., Homogeneous chemiluminescent assays for free choline in human plasma and whole blood. Anal Chim Acta. Oct. 2, 2006;579(1):61-7.

Altschul et al., Gapped BLAST and PSI-BLAST: a new generation of protein database search programs. Nucleic Acids Res. Sep. 1, 1997;25(17):3389-402.

Altschul, S.F. et al., Basic local alignment search tool. J Mol Biol. Oct. 5, 1990;215(3):403-10.

Beigert, A. et al., Sequence context-specific profiles for homology searching. Proc Natl Acad Sci U S A. Mar. 10, 2009;106(10):3770-5.

Braasch et al., Novel antisense and peptide nucleic acid strategies for controlling gene expression. Biochemistry. Apr. 9, 2002;41(14):4503-10.

Braitbard, et al., Competition between bound and free peptides in an ELISA-based procedure that assays peptides derived from protein digests. Proteome Sci. May 31, 2006;4:12.

Burbelo, P.D. et al. et al. Detection of Nucleocapsid Antibody to SARS-CoV-2 is More Sensitive than Antibody to Spike Protein in COVID-19 Patients. medRxiv. Preprint. Apr. 24, 2020; 1-24.

David, et al., Protein iodination with solid state lactoperoxidase. Biochemistry. Feb. 26, 1974;13(5):1014-21.

Durbin, et al., eds., Biological Sequence Analysis: Probabilistic Models of Proteins and Nucleic Acids, Cambridge University Press, Cambridge, UK (2009). Table of Contents.

Heller, A. Electrical wiring of redox enzymes. Acc. Chem. Res. 1990, 23, 5, 128-134.

Holliger, et al., Engineered antibody fragments and the rise of single domains. Nat Biotechnol. Sep. 2005;23(9):1126-36.

Holt, et al. Domain antibodies: proteins for therapy. Trends Biotechnol. Nov. 2003;21(11):484-90.

Hunter, et al., Preparation of Iodine-131 labelled human growth hormone of high specific activity. Nature, 194: (1962); 495-6.

Janeway, C. A. et al. (eds.), Immunobiology, 5th Ed., Garland Publishing, New York, N.Y. (2001). Table of Contents.

Kaufman, et al., Amplification and expression of sequences cotransfected with a modular dihydrofolate reductase complementary dna gene. J Mol Biol. Aug. 25, 1982;159(4):601-21.

Lehninger, A.L. Principles of Biochemistry, at 793-800 (Worth Pub. 1982).

Leung, D.T.M. et al. Antibody response of patients with severe acute respiratory syndrome (SARS) targets the viral nucleocapsid. J Infect Dis. Jul. 15, 2004;190(2):379-86.

Nygren, J. Conjugation of horseradish peroxidase to Fab fragments with different homobifunctional and heterobifunctional cross-linking reagents. A comparative study. J Histochem Cytochem. May 1982;30(5):407-12.

Pain, et al., Preparation of protein A-peroxidase monoconjugate using a heterobifunctional reagent, and its use in enzyme immunoassays. J Immunol Methods. 1981;40(2):219-30.

Soding, Protein homology detection by HMM-HMM comparison. Bioinformatics. Apr. 1, 2005;21(7):951-60.

Stoel, M. et al. Restricted IgA repertoire in both B-1 and B-2 cell-derived gut plasmablasts. J Immunol. Jan. 15, 2005;174(2):1046-54.

Urlaub, et al. Isolation of Chinese hamster cell mutants deficient in dihydrofolate reductase activity. Proc Natl Acad Sci U S A. Jul. 1980;77(7):4216-20.

Wahlestedt, et al., Potent and nontoxic antisense oligonucleotides containing locked nucleic acids. Proc Natl Acad Sci U S A. May 9, 2000;97(10):5633-8.

Walls, A.C. et al., Structure, Function, and Antigenicity of the SARS-CoV-2 Spike Glycoprotein. vol. 181, Issue 2, Apr. 16, 2020, pp. 281-292.e6.

Wang, J. Cyclohexene Nucleic Acids (CeNA): Serum Stable Oligonucleotides that Activate RNase H and Increase Duplex Stability with Complementary RNA. J. Am. Chem. Soc. 2000, 122, 36, 8595-8602.

Wrapp, D. et al. Cryo-EM structure of the 2019-nCOV spike in the prefusion conformation. Science. Mar. 13, 2020;367(6483):1260-1263.

Wu, C., et al., Simultaneous targeting of multiple disease mediators by a dual-variable-domain immunoglobulin. Nat Biotechnol. Nov. 2007;25(11):1290-7.

* cited by examiner

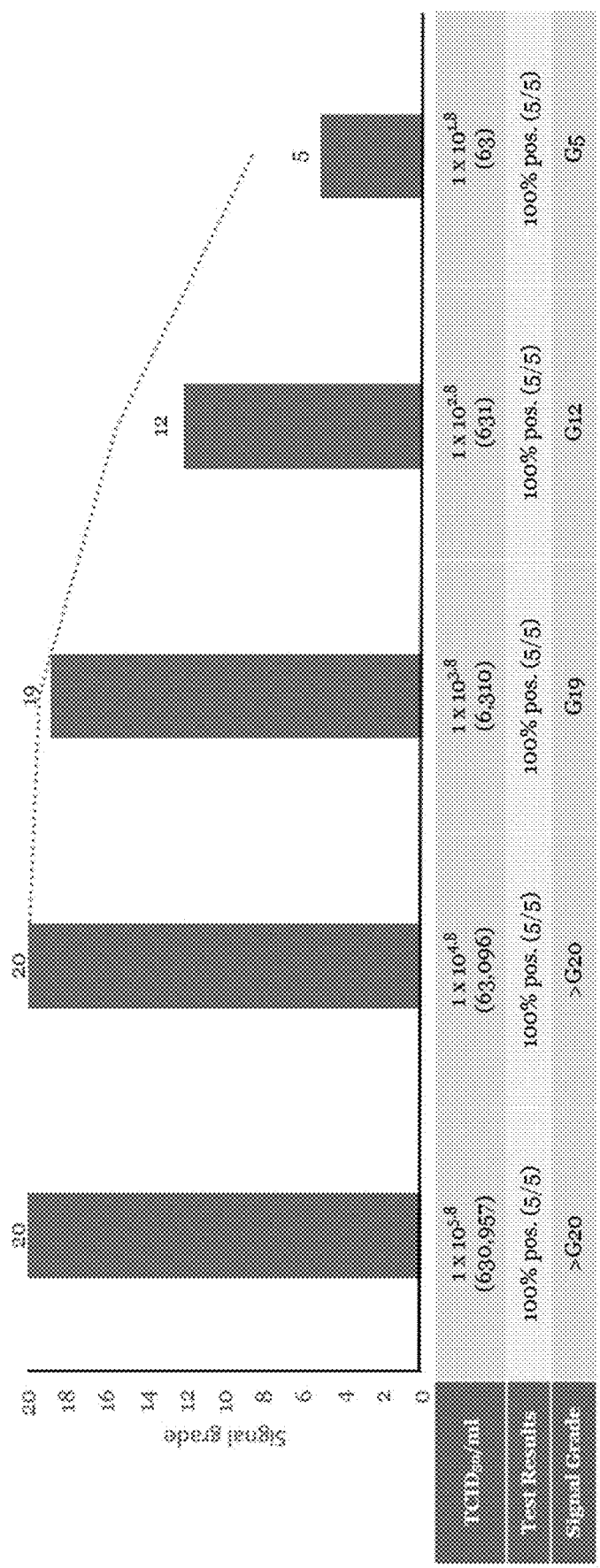

SEQUENCE LISTING

```
<160> NUMBER OF SEQ ID NOS: 18

<210> SEQ ID NO 1
<211> LENGTH: 15
<212> TYPE: PRT
<213> ORGANISM: Artificial sequence
<220> FEATURE:
<223> OTHER INFORMATION: Synthetic peptide

<400> SEQUENCE: 1

Cys Lys Ala Ser Gly Tyr Ser Phe Thr Ser Tyr Trp Met His Trp
1               5                   10                  15

<210> SEQ ID NO 2
<211> LENGTH: 18
<212> TYPE: PRT
<213> ORGANISM: Artificial sequence
<220> FEATURE:
<223> OTHER INFORMATION: Synthetic peptide

<400> SEQUENCE: 2

Met Ile Asp Pro Ser Asp Ser Glu Thr Arg Leu Asn Gln Arg Phe Lys
1               5                   10                  15

Asp Lys

<210> SEQ ID NO 3
<211> LENGTH: 15
<212> TYPE: PRT
<213> ORGANISM: Artificial sequence
<220> FEATURE:
<223> OTHER INFORMATION: Synthetic peptide

<400> SEQUENCE: 3

Cys Ala Arg Ser Leu Leu Arg Gly Val Tyr Ala Met Asp Tyr Trp
```

<210> SEQ ID NO 4
<211> LENGTH: 13
<212> TYPE: PRT
<213> ORGANISM: Artificial sequence
<220> FEATURE:
<223> OTHER INFORMATION: Synthetic peptide

<400> SEQUENCE: 4

Cys Lys Ala Ser Gln Ser Val Ser Asn Asp Val Ala Trp
1               5                   10

<210> SEQ ID NO 5
<211> LENGTH: 13
<212> TYPE: PRT
<213> ORGANISM: Artificial sequence
<220> FEATURE:
<223> OTHER INFORMATION: Synthetic peptide

<400> SEQUENCE: 5

Tyr Tyr Ala Ser Asn Arg Tyr Thr Gly Val Pro Asp Arg
1               5                   10

<210> SEQ ID NO 6
<211> LENGTH: 11
<212> TYPE: PRT
<213> ORGANISM: Artificial sequence
<220> FEATURE:
<223> OTHER INFORMATION: Synthetic peptide

<400> SEQUENCE: 6

Cys Gln Gln Asp Tyr Ser Ser Pro Tyr Thr Phe
1               5                   10

<210> SEQ ID NO 7
<211> LENGTH: 120
<212> TYPE: PRT
<213> ORGANISM: Artificial sequence
<220> FEATURE:
<223> OTHER INFORMATION: Synthetic peptide

<400> SEQUENCE: 7

Gln Val Gln Leu Gln Gln Ser Gly Pro Gln Leu Val Arg Pro Gly Ala
1               5                   10                  15

Ser Val Lys Ile Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Met Ile Asp Pro Ser Asp Ser Glu Thr Arg Leu Asn Gln Arg Phe
    50                  55                  60

Lys Asp Lys Ala Thr Leu Thr Val Asp Arg Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Ser Leu Leu Arg Gly Val Tyr Ala Met Asp Tyr Trp Gly Gln
            100                 105                 110

Gly Thr Ser Val Thr Val Ser Ser
        115                 120

<210> SEQ ID NO 8
<211> LENGTH: 107
<212> TYPE: PRT

<213> ORGANISM: Artificial sequence
<220> FEATURE:
<223> OTHER INFORMATION: Synthetic peptide

<400> SEQUENCE: 8

```
Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
            100                 105
```

<210> SEQ ID NO 9
<211> LENGTH: 5
<212> TYPE: PRT
<213> ORGANISM: Artificial sequence
<220> FEATURE:
<223> OTHER INFORMATION: Synthetic peptide

<400> SEQUENCE: 9

```
Ser Tyr Ala Ile Ser
1               5
```

<210> SEQ ID NO 10
<211> LENGTH: 17
<212> TYPE: PRT
<213> ORGANISM: Artificial sequence
<220> FEATURE:
<223> OTHER INFORMATION: Synthetic peptide

<400> SEQUENCE: 10

```
Gly Ile Ile Pro Ile Phe Gly Thr Ala Asn Tyr Ala Gln Lys Phe Gln
1               5                   10                  15

Gly
```

<210> SEQ ID NO 11
<211> LENGTH: 14
<212> TYPE: PRT
<213> ORGANISM: Artificial sequence
<220> FEATURE:
<223> OTHER INFORMATION: Synthetic peptide

<400> SEQUENCE: 11

```
Gly Tyr Trp Gly Ser Gly Tyr His Tyr Tyr Gly Met Asp Val
1               5                   10
```

<210> SEQ ID NO 12
<211> LENGTH: 11
<212> TYPE: PRT
<213> ORGANISM: Artificial sequence
<220> FEATURE:
<223> OTHER INFORMATION: Synthetic peptide

<400> SEQUENCE: 12

```
Gly Gly Asn Asn Ile Gly Ser Lys Ser Val His
```

<210> SEQ ID NO 13
<211> LENGTH: 7
<212> TYPE: PRT
<213> ORGANISM: Artificial sequence
<220> FEATURE:
<223> OTHER INFORMATION: Synthetic peptide

<400> SEQUENCE: 13

Tyr Asp Ser Asp Arg Pro Ser
1               5

<210> SEQ ID NO 14
<211> LENGTH: 11
<212> TYPE: PRT
<213> ORGANISM: Artificial sequence
<220> FEATURE:
<223> OTHER INFORMATION: Synthetic peptide

<400> SEQUENCE: 14

Gln Val Trp Asp Arg Ser Ser Asp Leu Val Val
1               5                   10

<210> SEQ ID NO 15
<211> LENGTH: 225
<212> TYPE: PRT
<213> ORGANISM: Artificial sequence
<220> FEATURE:
<223> OTHER INFORMATION: Synthetic peptide

<400> SEQUENCE: 15

Glu Val Gln Leu Val Glu Ser Gly Gly Gly Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Trp Gly Ser Gly Tyr His Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Cys
225

<210> SEQ ID NO 16
<211> LENGTH: 214
<212> TYPE: PRT
<213> ORGANISM: Artificial sequence
<220> FEATURE:
<223> OTHER INFORMATION: Synthetic peptide

<400> SEQUENCE: 16

Asp Ile Gln Met Thr Gln Ser Pro Ser Ser Val Ala Pro Gly Lys
1               5                   10                  15

Thr Ala Arg Ile Pro Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Arg Ser Ser Asp Leu
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ser Ser
    210

<210> SEQ ID NO 17
<211> LENGTH: 222
<212> TYPE: PRT
<213> ORGANISM: Artificial sequence
<220> FEATURE:
<223> OTHER INFORMATION: Synthetic peptide

<400> SEQUENCE: 17

Gln Val Gln Leu Gln Gln Ser Gly Pro Gln Leu Val Arg Pro Gly Ala
1               5                   10                  15

Ser Val Lys Ile Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Met Ile Asp Pro Ser Asp Ser Glu Thr Arg Leu Asn Gln Arg Phe
    50                  55                  60

Lys Asp Lys Ala Thr Leu Thr Val Asp Arg Ser Ser Ser Thr Ala Tyr

Met Gln Leu Ser Ser Pro Thr Ser Glu Asp Ser Ala Val Tyr Tyr Cys
65                  70                  75                  80

Ala Arg Ser Leu Leu Arg Gly Val Tyr Ala Met Asp Tyr Trp Gly Gln
                85                  90                  95

Gly Thr Ser Val Thr Val Ser Ser Ala Lys Thr Thr Pro Pro Ser Val
            100                 105                 110

Tyr Pro Leu Ala Pro Gly Ser Ala Ala Gln Thr Asn Ser Met Val Thr
        115                 120                 125

Leu Gly Cys Leu Val Lys Gly Tyr Phe Pro Glu Pro Val Thr Val Thr
    130                 135                 140

Trp Asn Ser Gly Ser Leu Ser Ser Gly Val His Thr Phe Pro Ala Val
145                 150                 155                 160

Leu Gln Ser Asp Leu Tyr Thr Leu Ser Ser Ser Val Thr Val Pro Ser
                165                 170                 175

Ser Thr Trp Pro Ser Glu Thr Val Thr Cys Asn Val Ala His Pro Ala
            180                 185                 190

Ser Ser Thr Lys Val Asp Lys Lys Ile Val Pro Arg Asp Cys
        195                 200                 205

210                 215                 220

<210> SEQ ID NO 18
<211> LENGTH: 214
<212> TYPE: PRT
<213> ORGANISM: Artificial sequence
<220> FEATURE:
<223> OTHER INFORMATION: Synthetic peptide

<400> SEQUENCE: 18

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

```
Thr Cys Glu Ala Thr His Lys Thr Ser Thr Ser Pro Ile Val Lys Ser
        195                 200                 205

Phe Asn Arg Asn Glu Ser
    210
```

ASSAYS FOR DETECTING SARS-COV-2

CROSS-REFERENCE TO RELATED APPLICATIONS

This application claims the benefit of U.S. Provisional Application Nos.: 63/060,975, filed Aug. 4, 2020; 63/065,898, filed Aug. 14, 2020; 63/067,051, filed Aug. 18, 2020; and 63/126,336, filed Dec. 16, 2020, the contents each of which are herein incorporated by reference in their entirety.

SEQUENCE LISTING STATEMENT

The text of the computer readable sequence listing filed herewith, titled "38691-205_SEQUENCE_LISTING_ST25", created Aug. 4, 2021, having a file size of 13,107 bytes, is hereby incorporated by reference in its entirety.

FIELD

The present disclosure relates to components and methods for detecting SARS-CoV-2 antigens.

BACKGROUND OF THE INVENTION

A novel coronavirus (SARS-CoV-2 (2019-nCoV)) emerged as a human pathogen in China's Hubei province in late 2019, causing fever, severe respiratory illness, and pneumonia. The disease associated with SARS-CoV-2 (2019-nCoV) was named COVID-19. The novel coronavirus is a member of the betacoronavirus genus, closely related to several bat coronaviruses and to severe acute respiratory syndrome coronavirus (SARS-CoV). However, unlike SARS-CoV, SARS-CoV-2 (2019-nCoV) is rapidly transmitted between humans.

As of the end of July 2021, over 190 million cases of COVID-19 were confirmed in over 200 countries, with complications of COVID-19 cited as the cause of death in over 4 million individuals. Because of the health risks imposed by SARS-CoV-2 transmission, there is a need for methods and kits to assess coronavirus transmission in humans, including methods to determine the presence and/or detect the amount of SARS-CoV-2 protein in one or more samples obtained from a subject.

SUMMARY OF THE INVENTION

The disclosure provides methods, devices, and kits for detecting the presence or determining the amount of SARS-CoV-2 in a sample from a subject.

In some embodiments, the methods comprise: contacting a sample obtained from a subject with a first antibody or antigen-binding fragment thereof which specifically binds to a protein from the SARS-CoV-2 virus, or a fragment thereof, under conditions which allow binding of the protein from the SARS-CoV-2 virus, or a fragment thereof, if present in the sample, to the first antibody or antigen-binding fragment thereof; contacting the sample with a conjugate comprising a second antibody which specifically binds to the protein from the SARS-CoV-2 virus, or a fragment thereof, and a detectable label; and assessing the presence of a signal from the detectable label, wherein the presence of a signal from the detectable label indicates the presence of the protein from the SARS-CoV-2 virus, or a fragment thereof in the sample.

In some embodiments, the protein from the SARS-CoV-2 virus, or a fragment thereof is the nucleocapsid (N) protein. The first antibody, or antigen-binding fragment thereof, and the second antibody, or antigen-binding fragment thereof, may recognize different epitopes of the protein from the SARS-CoV-2 virus (e.g., SARS-CoV-2 virus nucleocapsid (N) protein).

The first antibody or antigen-binding fragment thereof may comprise: (i) a heavy chain variable region comprising a complementarity determining region 1 (CDR) amino acid sequence having at least 70% identity to SEQ ID NO: 1, a CDR2 amino acid sequence having at least 70% identity to SEQ ID NO: 2, and a CDR3 amino acid sequence having at least 70% identity to SEQ ID NO: 3, and (ii) a light chain variable region comprising a CDR1 amino acid sequence having at least 70% identity to SEQ ID NO: 4, a CDR2 amino acid sequence having at least 70% identity to SEQ ID NO: 5, and a CDR3 amino acid sequence having at least 70% identity to SEQ ID NO: 6. In some embodiments, the first antibody or antigen-binding fragment thereof comprises a heavy chain variable region amino acid sequence having at least 70% identity to SEQ ID NO: 7 and a light chain variable region amino acid sequence having at least 70% identity to SEQ ID NO: 8. In some embodiments, the first antibody or antigen-binding fragment thereof comprises a heavy chain variable region amino acid sequence having at least 70% identity to SEQ ID NO: 17 and a light chain variable region amino acid sequence having at least 70% identity to SEQ ID NO: 18.

The second antibody or antigen-binding fragment thereof may comprise: (i) a heavy chain variable region comprising a complementarity determining region 1 (CDR) amino acid sequence having at least 70% identity to SEQ ID NO: 9, a CDR2 amino acid sequence having at least 70% identity to SEQ ID NO: 10, and a CDR3 amino acid sequence having at least 70% identity to SEQ ID NO: 11, and (ii) a light chain variable region comprising a CDR1 amino acid sequence having at least 70% identity to SEQ ID NO: 12, a CDR2 amino acid sequence having at least 70% identity to SEQ ID NO: 13, and a CDR3 amino acid sequence having at least 70% identity to SEQ ID NO: 14. In some embodiments, the second antibody or antigen-binding fragment thereof comprises a heavy chain variable region amino acid sequence having at least 70% identity to SEQ ID NO: 15 and a light chain variable region amino acid sequence having at least 70% identity to SEQ ID NO: 16.

In some embodiments, the methods are performed using an immunoassay. The immunoassay may be an enzyme-linked immunosorbent assay (ELISA) or a lateral flow immunoassay (LFA).

The sample may be any sample from a subject comprising or suspected of comprising SARS-CoV02. In some embodiments, the sample comprises a nasal or nasopharyngeal swab or brush, saliva, mucus, blood, serum, or plasma.

Also disclosed herein are lateral flow devices comprising: a first antibody, or antigen-binding fragment thereof, which specifically binds to a protein from the SARS-CoV-2 virus, or a fragment thereof and a second antibody, or antigen-binding fragment thereof, which specifically binds to a protein from the SARS-CoV-2 virus, or a fragment thereof. In some embodiments, the first antibody, or antigen-binding fragment thereof, is immobilized. In some embodiments, a test line comprises the first antibody, or antigen-binding fragment thereof. In some embodiments the second antibody, or antigen-binding fragment thereof, comprises a detectable label. In some embodiments, a sample pad comprises the second antibody, or antigen-binding fragment thereof.

In some embodiments, the protein from the SARS-CoV-2 virus, or a fragment thereof is the nucleocapsid (N) protein. The first antibody, or antigen-binding fragment thereof, and the second antibody, or antigen-binding fragment thereof, may recognize different epitopes of the protein from the SARS-CoV-2 virus (e.g., SARS-CoV-2 virus nucleocapsid (N) protein).

The first antibody or antigen-binding fragment thereof may comprise: (i) a heavy chain variable region comprising a complementarity determining region 1 (CDR) amino acid sequence having at least 70% identity to SEQ ID NO: 1, a CDR2 amino acid sequence having at least 70% identity to SEQ ID NO: 2, and a CDR3 amino acid sequence having at least 70% identity to SEQ ID NO: 3, and (ii) a light chain variable region comprising a CDR1 amino acid sequence having at least 70% identity to SEQ ID NO: 4, a CDR2 amino acid sequence having at least 70% identity to SEQ ID NO: 5, and a CDR3 amino acid sequence having at least 70% identity to SEQ ID NO: 6. In some embodiments, the first antibody or antigen-binding fragment thereof comprises a heavy chain variable region amino acid sequence having at least 70% identity to SEQ ID NO: 7 and a light chain variable region amino acid sequence having at least 70% identity to SEQ ID NO: 8. In some embodiments, the first antibody or antigen-binding fragment thereof comprises a heavy chain variable region amino acid sequence having at least 70% identity to SEQ ID NO: 17 and a light chain variable region amino acid sequence having at least 70% identity to SEQ ID NO: 18.

The second antibody or antigen-binding fragment thereof may comprise: (i) a heavy chain variable region comprising a complementarity determining region 1 (CDR) amino acid sequence having at least 70% identity to SEQ ID NO: 9, a CDR2 amino acid sequence having at least 70% identity to SEQ ID NO: 10, and a CDR3 amino acid sequence having at least 70% identity to SEQ ID NO: 11, and (ii) a light chain variable region comprising a CDR1 amino acid sequence having at least 70% identity to SEQ ID NO: 12, a CDR2 amino acid sequence having at least 70% identity to SEQ ID NO: 13, and a CDR3 amino acid sequence having at least 70% identity to SEQ ID NO: 14. In some embodiments, the second antibody or antigen-binding fragment thereof comprises a heavy chain variable region amino acid sequence having at least 70% identity to SEQ ID NO: 15 and a light chain variable region amino acid sequence having at least 70% identity to SEQ ID NO: 16.

Further disclosed are kits comprising the lateral flow device described herein. The kits may further comprise at least one or both of an extraction buffer and a sampling device (e.g., a nasal swab)

Other aspects and embodiments of the disclosure will be apparent in light of the following detailed description and accompanying FIGURES.

BRIEF DESCRIPTION OF THE DRAWINGS

FIG. 1 is a graph of a dose response of an exemplary lateral flow assay to test for a hook effect.

DETAILED DESCRIPTION OF THE INVENTION

The present disclosure is predicated, at least in part, on the development of a method with a pair of antibodies which allow detection of SARS-CoV-2 with increased specificity and lower limits of detection.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "immunoglobulin" or "antibody," as used herein, refers to a protein that is found in blood or other bodily fluids of vertebrates, which is used by the immune system to identify and neutralize foreign objects, such as bacteria and viruses. Typically, an immunoglobulin or antibody is a protein that comprises at least one complementarity determining region (CDR). The CDRs form the "hypervariable region" of an antibody, which is responsible for antigen binding (discussed further below). A whole immunoglobulin typically consists of four polypeptides: two identical copies of a heavy (H) chain polypeptide and two identical copies of a light (L) chain polypeptide. Each of the heavy chains contains one N-terminal variable ($V_H$) region and three C-terminal constant ($C_{H1}$, $C_{H2}$, and $C_{H3}$) regions, and each light chain contains one N-terminal variable ($V_L$) region and one C-terminal constant ($C_L$) region. The light chains of antibodies can be assigned to one of two distinct types, either kappa (κ) or lambda (λ), based upon the amino acid sequences of their constant domains. In a typical immunoglobulin, each light chain is linked to a heavy chain by disulfide bonds, and the two heavy chains are linked to each other by disulfide bonds. The light chain variable region is aligned with the variable region of the heavy chain, and the light chain constant region is aligned with the first constant region of the heavy chain. The remaining constant regions of the heavy chains are aligned with each other.

The variable regions of each pair of light and heavy chains form the antigen binding site of an antibody. The $V_H$ and $V_L$ regions have the same general structure, with each region comprising four framework (FW or FR) regions. The term "framework region," as used herein, refers to the relatively conserved amino acid sequences within the variable region which are located between the CDRs. There are four framework regions in each variable domain, which are designated FR1, FR2, FR3, and FR4. The framework regions form the β sheets that provide the structural framework of the variable region (see, e.g., C. A. Janeway et al. (eds.), *Immunobiology*, 5th Ed., Garland Publishing, New York, N.Y. (2001)).

The framework regions are connected by three CDRs. As discussed above, the three CDRs, known as CDR1, CDR2, and CDR3, form the "hypervariable region" of an antibody, which is responsible for antigen binding. The CDRs form loops connecting, and in some cases comprising part of, the beta-sheet structure formed by the framework regions. While the constant regions of the light and heavy chains are not directly involved in binding of the antibody to an antigen, the constant regions can influence the orientation of the variable regions. The constant regions also exhibit various effector functions, such as participation in antibody-dependent complement-mediated lysis or antibody-dependent cellular toxicity via interactions with effector molecules and cells.

As used herein, when an antibody or other entity (e.g., antigen binding domain) "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ $M^{-1}$ (e.g., $>10^7$ $M^{-1}$, $>10^8$ $M^{-1}$, $>10^9 M^{-1}$, $>10^{10}$ $M^{-1}$, $>10^{11}$ $M^{-1}$, $>10^{12}$ $M^{-1}$, $>10^{13}$ $M^{-1}$, etc.). In certain such embodiments, an antibody is capable of binding different antigens so long as the different antigens comprise that particular epitope. In certain instances, for example, homologous proteins from different species may comprise the same epitope.

"Antibody" and "antibodies" as used herein refers to monoclonal antibodies, monospecific antibodies (e.g., which can either be monoclonal, or may also be produced by other means than producing them from a common germ cell), multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain variable fragments ("scFv"), single chain antibodies, single domain antibodies, Fab fragments, F(ab') fragments, F(ab')$_2$ fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., *Nature Biotechnology*, 25(11):1290-1297 (2007) and PCT International Application WO 2001/058956, the contents of each of which are herein incorporated by reference), or domain antibodies (dAbs) (e.g., such as described in Holt et al. (2014) *Trends in Biotechnology* 21:484-490), and including single domain antibodies sdAbs that are naturally occurring, e.g., as in cartilaginous fishes and camelid, or which are synthetic, e.g., nanobodies, VHH, or other domain structure), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass. For simplicity sake, an antibody against an analyte is frequently referred to herein as being either an "anti-analyte antibody" or merely an "analyte antibody".

The terms "fragment of an antibody," "antibody fragment," and "antigen-binding fragment" of an antibody are used interchangeably herein to refer to one or more fragments of an antibody that retain the ability to specifically bind to an antigen (see, generally, Holliger et al., Nat. Biotech., 23(9): 1126-1129 (2005)). Any antigen-binding fragment of the antibody described herein is within the scope of the invention. The antibody fragment desirably comprises, for example, one or more CDRs, the variable region (or portions thereof), the constant region (or portions thereof), or combinations thereof. In some embodiments, the portion does not include the constant heavy chain domains (i.e., CH2, CH3, or CH4, depending on the antibody isotype) of the Fc region of the intact antibody. Examples of antibody fragments include, but are not limited to, (i) a Fab fragment, which is a monovalent fragment consisting of the $V_L$, $V_H$, $C_L$, and $C_{H1}$ domains, (ii) a F(ab')$_2$ fragment, which is a bivalent fragment comprising two Fab fragments linked by a disulfide bridge at the hinge region, (iii) a Fv fragment consisting of the $V_L$ and $V_H$ domains of a single arm of an antibody, (iv) a Fab' fragment, which results from breaking the disulfide bridge of an F(ab')2 fragment using mild reducing conditions, (v) a disulfide-stabilized Fv fragment (dsFv), (vi) a domain antibody (dAb), which is an antibody single variable region domain ($V_H$ or $V_L$) polypeptide that specifically binds antigen, (vii) Fab'-SH fragments, (viii) Fd fragments, (ix) diabodies, (x) single-chain Fv (scFv) molecules, (xi) single-chain polypeptides containing only one light chain variable domain, (xii) single-chain polypeptides containing the three CDRs of the light-chain variable domain, (xii) single-chain polypeptides containing only one heavy chain variable region, and (xiii) single-chain polypeptides containing the three CDRs of the heavy chain variable region.

Antibody fragments that recognize specific epitopes may be generated by known techniques. For example, Fab and F(ab')$_2$ fragments may be produced by proteolytic cleavage of immunoglobulin molecules, using enzymes such as papain (to produce two identical Fab fragments) or pepsin (to produce an F(ab')$_2$ fragment). A F(ab')$_2$ fragment of an IgG molecule retains the two antigen-binding sites of the larger ("parent") IgG molecule, including both light chains (containing the variable light chain and constant light chain regions), the CH1 domains of the heavy chains, and a disulfide-forming hinge region of the parent IgG molecule. Accordingly, an F(ab')$_2$ fragment is still capable of cross-linking antigen molecules like the parent IgG molecule.

"Fragment antigen-binding fragment" or "Fab fragment" as used herein refers to a fragment of an antibody that binds to antigens and that contains one antigen-binding site, one complete light chain, and part of one heavy chain. Fab is a monovalent fragment consisting of the $V_L$, $V_H$, $C_L$ and $C_{H1}$ domains. Fab is composed of one constant and one variable domain of each of the heavy and the light chain. The variable domain contains the paratope (the antigen-binding site), comprising a set of complementarity determining regions, at the amino terminal end of the monomer. Each arm of the Y thus binds an epitope on the antigen. Fab fragments can be generated such as has been described in the art, e.g., using the enzyme papain, which can be used to cleave an immunoglobulin monomer into two Fab fragments and an Fc fragment, or can be produced by recombinant means.

"F(ab')$_2$ fragment" as used herein refers to antibodies generated by pepsin digestion of whole IgG antibodies to remove most of the Fc region while leaving intact some of the hinge region. F(ab')$_2$ fragments have two antigen-binding F(ab) portions linked together by disulfide bonds, and therefore are divalent with a molecular weight of about 110 kDa. Divalent antibody fragments (F(ab')$_2$ fragments) are smaller than whole IgG molecules and enable a better penetration into tissue thus facilitating better antigen recognition in immunohistochemistry. The use of F(ab')$_2$ fragments also avoids nonspecific binding to Fc receptor on live cells or to Protein A/G. F(ab')$_2$ fragments can both bind and precipitate antigens.

"Framework" (FR) or "Framework sequence" as used herein may mean the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region.

Human heavy chain and light chain FR sequences are known in the art that can be used as heavy chain and light chain "acceptor" framework sequences (or simply, "acceptor" sequences) to humanize a non-human antibody using techniques known in the art. In one embodiment, human heavy chain and light chain acceptor sequences are selected from the framework sequences listed in publicly available databases such as V-base (hypertext transfer protocol: vbase (dot)mrc-cpe(dot)cam(dot)ac(dot)uk) or in the international ImMunoGeneTics® (IMGT®) information system (hypertext transfer protocol:imgt(dot)cines(dot)fr/texts/IMGTrepertoire/LocusGenes/).

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multi-valent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., *Nature Biotechnology*, 25:1290-1297 (2007)).

The terms "nucleic acid," "polynucleotide," "nucleotide sequence," and "oligonucleotide" are used interchangeably herein and refer to a polymer or oligomer of pyrimidine and/or purine bases, preferably cytosine, thymine, and uracil, and adenine and guanine, respectively (See Albert L. Lehninger, *Principles of Biochemistry*, at 793-800 (Worth Pub. 1982)). The terms encompass any deoxyribonucleotide, ribonucleotide, or peptide nucleic acid component, and any chemical variants thereof, such as methylated, hydroxymethylated, or glycosylated forms of these bases. The polymers or oligomers may be heterogenous or homogenous in composition, may be isolated from naturally occurring sources, or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. In some embodiments, a nucleic acid or nucleic acid sequence comprises other kinds of nucleic acid structures such as, for instance, a DNA/RNA helix, peptide nucleic acid (PNA), morpholino nucleic acid (see, e.g., Braasch and Corey, *Biochemistry*, 41(14): 4503-4510 (2002) and U.S. Pat. No. 5,034,506), locked nucleic acid (LNA; see Wahlestedt et al., *Proc. Natl. Acad. Sci. U.S.A.*, 97: 5633-5638 (2000)), cyclohexenyl nucleic acids (see Wang, *J. Am. Chem. Soc.*, 122: 8595-8602 (2000)), and/or a ribozyme. The terms "nucleic acid" and "nucleic acid sequence" may also encompass a chain comprising non-natural nucleotides, modified nucleotides, and/or non-nucleotide building blocks that can exhibit the same function as natural nucleotides (e.g., "nucleotide analogs").

The terms "peptide," "polypeptide," and "protein" are used interchangeably herein and refer to a polymeric form of amino acids of any length, which can include coded and non-coded amino acids, chemically or biochemically modified or derivatized amino acids, and polypeptides having modified peptide backbones.

The terms "immunogen" and "antigen" are used interchangeably herein and refer to any molecule, compound, or substance that induces an immune response in an animal (e.g., a mammal). An "immune response" can entail, for example, antibody production and/or the activation of immune effector cells. An antigen in the context of the disclosure can comprise any subunit, fragment, or epitope of any proteinaceous or non-proteinaceous (e.g., carbohydrate or lipid) molecule that provokes an immune response in a mammal. By "epitope" is meant a sequence of an antigen that is recognized by an antibody or an antigen receptor. Epitopes also are referred to in the art as "antigenic determinants." In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three-dimensional structural characteristics (e.g., a "conformational" epitope) and/or specific charge characteristics. The antigen can be a protein or peptide of viral, bacterial, parasitic, fungal, protozoan, prion, cellular, or extracellular origin, which provokes an immune response in a mammal, preferably leading to protective immunity.

The terms "detectable label" and "label," as used herein, refer to a moiety that can produce a signal that is detectable by visual or instrumental means. In some embodiments, the label is a direct label, e.g., an entity that, in its natural state, is readily visible either to the naked eye or with the aid of an optical filter and/or applied stimulation, e.g., UV light to promote fluorescence. For example, minute colored particles, such as dye sols, metallic sols (e.g., gold), and colored latex particles, are very suitable. In some embodiments, the label is an indirect label such as enzymes, e.g., alkaline phosphatase and horseradish peroxidase. Indirect labels usually require the addition of one or more developing reagents such as substrates before a visible signal can be detected.

As used herein, the word "presence" or "absence" (or, alternatively, "present" or "absent") is used in a relative sense to describe the amount or level of a particular entity (e.g., an analyte). For example, when an analyte is said to be "present" in a test sample, it means the level or amount of this analyte is above a pre-determined threshold; conversely, when an analyte is said to be "absent" in a test sample, it means the level or amount of this analyte is below a pre-determined threshold. The pre-determined threshold may be the threshold for detectability associated with the particular test used to detect the analyte or any other threshold. When an analyte is "detected" in a sample it is "present" in the sample; when an analyte is "not detected"

it is "absent" from the sample. Further, a sample in which an analyte is "detected" or in which the analyte is "present" is a sample that is "positive" for the analyte. A sample in which an analyte is "not detected" or in which the analyte is "absent" is a sample that is "negative" for the analyte.

As used herein, the term "analyte" refers to a compound or composition to be detected and/or measured by specific binding to a ligand, receptor, or enzyme (e.g., an antibody or antigen). In some embodiments, the analyte is a protein or a nucleic acid. In some embodiments, the analyte is an antigen. In some embodiments, the analyte is a fragment of an antigen. In some embodiments, the analyte is an analyte analogue or an analyte derivative (e.g., an analyte altered by chemical or biological methods). In some embodiments, an analyte is an epitope. In some embodiments, the term "analyte" refers to a protein and/or a nucleic acid from the SARS-CoV-2 virus. In some embodiments, the analyte is a fragment and/or epitope of a protein and/or nucleic acid from the SARS-CoV-2 virus. In some embodiments, the analyte is the SARS-CoV-2 spike protein ("S" protein as provided by UniProtKB Accession Number P0DTC2) or the spike protein receptor-binding domain (see, e.g., Wrapp (2020) "Cryo-EM structure of the 2019-nCoV spike in the prefusion conformation" Science 367: 1260-63; Walls (2020) "Structure, Function, and Antigenicity of the SARSCoV-2 Spike Glycoprotein" Cell 180: 1-12, each of which is incorporated herein by reference). In some embodiments, the analyte is a viral transcription and/or replication protein (e.g., replicase polyprotein 1a (R1a) as provided by UniProtKB Accession Number P0DTC1 or replicase polyprotein 1ab (R1ab) as provided by UniProtKB Accession Number P0DTD1. In some embodiments, the analyte is a viral budding protein (e.g., protein 3a as provided by UniProtKB Accession Number P0DTC3 or envelope small membrane protein (E) as provided by P0DTC4). In some embodiments, the analyte is a virus morphogenesis protein (e.g., membrane protein (M) as provided by UniProtKB Accession Number P0DTC5). In some embodiments, the analyte is non-structural protein 6 (e.g., as provided by UniProtKB Accession Number P0DTC6), protein 7a (NS7A) (e.g., as provided by UniProtKB Accession Number P0DTC7), protein 7b (NS7B) (e.g., as provided by UniProtKB Accession Number P0DTD8), non-structural protein 8 (NS8) (e.g., as provided by UniProtKB Accession Number P0DTC8), or protein 9b (e.g., as provided by UniProtKB Accession Number P0DTD2). In some embodiments, the analyte is a viral genome packaging protein (e.g., nucleoprotein (e.g., N), e.g., as provided by UniProtKB Accession Number P0DTC9). In some embodiments, the analyte is an uncharacterized protein (e.g., as provided by UniProtKB Accession Number P0DTD3 or A0A663DJA2).

As used herein, a "system" refers to a plurality of real and/or abstract components operating together for a common purpose. In some embodiments, a "system" is an integrated assemblage of hardware and/or software components. In some embodiments, each component of the system interacts with one or more other components and/or is related to one or more other components. In some embodiments, a system refers to a combination of components and software for controlling and directing methods.

As used herein, the term "sample" refers to any sample comprising SARS-CoV-2 or a part or component thereof or that potentially comprises SARS-CoV-2 or a part or component thereof. Accordingly, the term "sample" refers to a material to be tested for the presence or amount of an analyte, e.g., SARS-CoV-2 or a part or component thereof. Preferably, a sample is a fluid sample, preferably a liquid sample. For example, a sample may be a bodily fluid such as blood (including for example, capillary blood, venous blood, dried blood spot, etc.), serum, plasma, ocular fluid, urine, mucus, semen, nasal or nasopharyngeal swab fluid, throat swab, tears, sweat, or saliva. Viscous liquid, semisolid, or solid specimens may be used to create liquid solutions, eluates, suspensions, or extracts that can be samples. For example, throat or genital swabs may be suspended in a liquid solution to make a sample.

"Point-of-care device" refers to a device used to provide medical diagnostic testing at or near the point-of-care (namely, outside of a laboratory), at the time and place of patient care (such as in a hospital, physician's office, urgent or other medical care facility, a patient's home, a nursing home and/or a long-term care and/or hospice facility). Examples of point-of-care devices include those produced by Abbott Laboratories (Abbott Park, IL) (e.g., i-STAT and i-STAT Alinity, Universal Biosensors (Rowville, Australia) (see US 2006/0134713), Axis-Shield PoC AS (Oslo, Norway) and Clinical Lab Products (Los Angeles, USA).

"Sensitivity" of an assay as used herein refers to the proportion of subjects for whom the outcome is positive that are correctly identified as positive (e.g., correctly identifying those subjects with a disease or medical condition for which they are being tested). For example, this might include correctly identifying subjects as having been infected with a coronavirus, such as a β-coronavirus, from those who do not or have not been infected with a coronavirus, such as a β-coronavirus. In some aspects, the sensitivity of an assay can be determined by evaluating changes in the signal to noise (S/N) ratio of the assay. For example, in some aspects, an increase in a S/N ratio may indicate an improvement in the sensitivity of an assay for a particular analyte (e.g., SARS-CoV-2 nucleocapsid protein).

"Specificity" of an assay as used herein refers to the proportion of subjects for whom the outcome is negative that are correctly identified as negative (e.g., correctly identifying those subjects who do not have a disease or medical condition for which they are being tested). For example, this might include correctly identifying subjects having being infected with a coronavirus, such as a β-coronavirus, from those who have not been infected with a coronavirus, such as a β-coronavirus.

Unless otherwise defined herein, scientific, and technical terms used in connection with the present disclosure shall have the meanings that are commonly understood by those of ordinary skill in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

1. ANTIBODIES

In accordance with the disclosed methods, a sample is contacted with a first antibody or antigen-binding fragment thereof (e.g., Fab) which specifically binds to a protein from the SARS-CoV-2 virus, or a fragment thereof and a second antibody or antigen-binding fragment thereof (e.g., Fab) which specifically binds to the protein from the SARS-CoV-2 virus. The first antibody, or antigen-binding fragment thereof, and the second antibody, or antigen-binding fragment thereof, recognize different epitopes of the protein from the SARS-CoV-2 virus, or fragment thereof. In some embodiments, the protein from the SARS-CoV-2 virus is a viral genome packaging protein (e.g., nucleocapsid (N) protein, e.g., as provided by UniProtKB Accession Number P0DTC9).

The first antibody or antigen-binding fragment thereof antibody comprises (i) a heavy chain variable region comprising a CDR1 amino acid sequence that is at least 70% (e.g. 75% 80%, 85%, 90%, 95%, 98%) identical to SEQ ID NO: 1, a CDR2 amino acid sequence that is at least 70% identical to SEQ ID NO: 2, and a CDR3 amino acid sequence that is at least 70% identical to SEQ ID NO: 3 and (ii) a light chain variable region comprising a CDR1 amino acid sequence that is at least 70% identical to SEQ ID NO: 4, a CDR2 amino acid sequence o that is at least 70% identical to SEQ ID NO: 5, and a CDR3 amino acid sequence that is at least 70% identical to SEQ ID NO: 6.

Alternatively, the first antibody or antigen-binding fragment thereof may comprise heavy chain variable region CDR1, CDR2, and CDR3 amino acid sequences that are at least 90% identical to SEQ ID NO: 1, SEQ ID NO: 2, and/or SEQ ID NO: 3, respectively, and/or light chain variable region CDR1, CDR2, and CDR3 amino acid sequences that are at least 90% identical to SEQ ID NO: 4, SEQ ID NO: 5, and/or SEQ ID NO: 6, respectively.

In one embodiment, (i) each of the heavy chain variable region CDR1, CDR2, and/or CDR3 amino acid sequences comprises, consists essentially of, or consists of SEQ ID NO: 1, SEQ ID NO: 2, and/or SEQ ID NO: 3, respectively, and (ii) each of the light chain variable region CDR1, CDR2, and/or CDR3 amino acid sequences comprises, consists essentially of, or consists of SEQ ID NO: 4, SEQ ID NO: 5, and/or SEQ ID NO: 6, respectively. When the heavy and/or light chain CDR1, CDR2, and CDR3 of the disclosed antibody consist essentially of the amino acid sequences set forth above, additional components can be included in the CDR that do not materially affect the antibody or antigen-binding fragment thereof (e.g., protein moieties such as biotin that facilitate purification or isolation). When the heavy and/or light chain CDR1, CDR2, and CDR3 of the disclosed antibody consist of the amino acid sequences set forth above, each CDR does not comprise any additional components (e.g., components that are not endogenous to the CDR).

```
                                           SEQ ID NO: 1
CKASGYSFTSYWMHW

SEQ ID NO: 2
MIDPSDSETRLNQRFKDK

SEQ ID NO: 3
CARSLLRGVYAMDYW

SEQ ID NO: 4
CKASQSVSNDVAW

SEQ ID NO: 5
YYASNRYTGVPDR

SEQ ID NO: 6
CQQDYSSPYTF
```

In some embodiments, the first antibody or antigen-binding fragment thereof comprises a heavy chain variable region ($V_H$) amino acid sequence comprising, consisting essentially of, or consisting of SEQ ID NO: 7 and a light chain variable region ($V_L$) amino acid sequence comprising, consisting essentially of, or consisting of SEQ ID NO: 8. When the $V_L$ amino acid sequence consists essentially of SEQ ID NO: 7 and the $V_L$ amino acid sequence consists essentially of SEQ ID NO: 8, additional components can be included in the heavy or light chain variable regions that do not materially affect the antibody or antigen-binding fragment thereof (e.g., protein moieties such as biotin or a His tag that facilitate purification or isolation). When the $V_L$ amino acid sequence consists of SEQ ID NO: 7 and the $V_L$ amino acid sequence consists of SEQ ID NO: 8, the heavy and light chain variable regions do not comprise any additional components (e.g., components that are not endogenous to the heavy or light chain variable region).

In other embodiments, the first antibody or antigen-binding fragment thereof may comprise a heavy chain variable region amino acid sequence that is at least 70% identical to SEQ ID NO: 7 and a light chain variable region amino acid sequence that is at least 70% to SEQ ID NO: 8.

```
                                           SEQ ID NO: 7
QVQLQQSGPQLVRPGASVKISCKASGYSFTSYWMHWVKQRPGQGLEWIG

MIDPSDSETRLNQRFKDKATLTVDRSSSTAYMQLSSPTSEDSAVYYCAR

SLLRGVYAMDYWGQGTSVTVSS

SEQ ID NO: 8
SIVMTQTPKFLLVSAGDRVTITCKASQSVSNDVAWYQQKPGQSPKLLIY

YASNRYTGVPDRFTGSGYGTDFTFTISTVQAEDLAVYFCQQDYSSPYTF

GGGTKLEIK
```

In some embodiments, the first antibody or antigen-binding fragment thereof comprises a heavy chain variable region ($V_H$) amino acid sequence comprising, consisting essentially of, or consisting of SEQ ID NO: 17 and a light chain variable region ($V_L$) amino acid sequence comprising, consisting essentially of, or consisting of SEQ ID NO: 18. When the $V_L$ amino acid sequence consists essentially of SEQ ID NO: 17 and the $V_L$ amino acid sequence consists essentially of SEQ ID NO: 18, additional components can be included in the heavy or light chain variable regions that do not materially affect the antibody or antigen-binding fragment thereof (e.g., protein moieties such as biotin or a His tag that facilitate purification or isolation). When the $V_L$ amino acid sequence consists of SEQ ID NO: 17 and the $V_L$ amino acid sequence consists of SEQ ID NO: 18, the heavy and light chain variable regions do not comprise any additional components (e.g., components that are not endogenous to the heavy or light chain variable region).

In other embodiments, the first antibody or antigen-binding fragment thereof may comprise a heavy chain variable region amino acid sequence that is at least 70% identical to SEQ ID NO: 17 and a light chain variable region amino acid sequence that is at least 70% to SEQ ID NO: 18.

```
                                          SEQ ID NO: 17
QVQLQQSGPQLVRPGASVKISCKASGYSFTSYWMHWVKQRPGQGLEWIG

MIDPSDSETRLNQRFKDKATLTVDRSSSTAYMQLSSPTSEDSAVYYCAR

SLLRGVYAMDYWGQGTSVTVSSAKTTPPSVYPLAPGSAAQTNSMVTLGC

LVKGYFPEPVTVTWNSGSLSSGVHTFPAVLQSDLYTLSSSVTVPSSTWP

SETVTCNVAHPASSTKVDKKIVPRDC
```

-continued

SEQ ID NO: 18
SIVMTQTPKFLLVSAGDRVTITCKASQSVSNDVAWYQQKPGQSPKLLIY
YASNRYTGVPDRFTGSGYGTDFTFTISTVQAEDLAVYFCQQDYSSPYTF
GGGTKLEIKRADAAPTVSIFPPSSEQLTSGGASVVCFLNNFYPKDINVK
WKIDGSERQNGVLNSWTDQDSKDSTYSMSSTLTLTKDEYERHNSYTCEA
THKTSTSPIVKSFNRNES

The second antibody or antigen-binding fragment thereof antibody comprises (i) a heavy chain variable region comprising a CDR1 amino acid sequence that is at least 70% (e.g. 75% 80%, 85%, 90%, 95%, 98%) identical to SEQ ID NO: 9, a CDR2 amino acid sequence that is at least 70% identical to SEQ ID NO: 10, and a CDR3 amino acid sequence that is at least 70% identical to SEQ ID NO: 11 and (ii) a light chain variable region comprising a CDR1 amino acid sequence that is at least 70% identical to SEQ ID NO: 12, a CDR2 amino acid sequence o that is at least 70% identical to SEQ ID NO: 13, and a CDR3 amino acid sequence that is at least 70% identical to SEQ ID NO: 14.

Alternatively, the second antibody or antigen-binding fragment thereof may comprise heavy chain variable region CDR1, CDR2, and CDR3 amino acid sequences that are at least 90% identical to SEQ ID NO: 9, SEQ ID NO: 10, and/or SEQ ID NO: 11, respectively, and/or light chain variable region CDR1, CDR2, and CDR3 amino acid sequences that are at least 90% identical to SEQ ID NO: 12, SEQ ID NO: 13, and/or SEQ ID NO: 14, respectively.

In one embodiment, (i) each of the heavy chain variable region CDR1, CDR2, and/or CDR3 amino acid sequences comprises, consists essentially of, or consists of SEQ ID NO: 9, SEQ ID NO: 10, and/or SEQ ID NO: 11, respectively, and (ii) each of the light chain variable region CDR1, CDR2, and/or CDR3 amino acid sequences comprises, consists essentially of, or consists of SEQ ID NO: 12, SEQ ID NO: 13, and/or SEQ ID NO: 14, respectively. When the heavy and/or light chain CDR1, CDR2, and CDR3 of the disclosed antibody consist essentially of the amino acid sequences set forth above, additional components can be included in the CDR that do not materially affect the antibody or antigen-binding fragment thereof (e.g., protein moieties such as biotin that facilitate purification or isolation). When the heavy and/or light chain CDR1, CDR2, and CDR3 of the disclosed antibody consist of the amino acid sequences set forth above, each CDR does not comprise any additional components (e.g., components that are not endogenous to the CDR).

SEQ ID NO: 9
SYAIS

SEQ ID NO: 10
GIIPIFGTANYAQKFQG

SEQ ID NO: 11
GYWGSGYHYYGMDV

SEQ ID NO: 12
GGNNIGSKSVH

SEQ ID NO: 13
YDSDRPS

SEQ ID NO: 14
QVWDRSSDLVV

In some embodiments, the second antibody or antigen-binding fragment thereof comprises a heavy chain variable region ($V_H$) amino acid sequence comprising, consisting essentially of, or consisting of SEQ ID NO: 15 and a light chain variable region ($V_L$) amino acid sequence comprising, consisting essentially of, or consisting of SEQ ID NO: 16. When the $V_L$ amino acid sequence consists essentially of SEQ ID NO: 15 and the $V_L$ amino acid sequence consists essentially of SEQ ID NO: 16, additional components can be included in the heavy or light chain variable regions that do not materially affect the antibody or antigen-binding fragment thereof (e.g., protein moieties such as biotin or His tag that facilitate purification or isolation). When the $V_L$ amino acid sequence consists of SEQ ID NO: 15 and the $V_L$ amino acid sequence consists of SEQ ID NO: 16, the heavy and light chain variable regions do not comprise any additional components (e.g., components that are not endogenous to the heavy or light chain variable region).

In other embodiments, the second antibody or antigen-binding fragment thereof may comprise a heavy chain variable region amino acid sequence that is at least 70% identical to SEQ ID NO: 15 and a light chain variable region amino acid sequence that is at least 70% to SEQ ID NO: 16.

SEQ ID NO: 15
EVQLVESGGGVKKPGSSVKVSCKASGGTFSSYAISWVRQAPGQGLEWM
GGIIPIFGTANYAQKFQGRVTITADESTSTAYMELSSLRSEDTAVYYC
ARGYWGSGYHYYGMDVWGQGTTVTVSSASTKGPSVFPLAPSSKSTSGG
TAALGCLVKDYFPEPVTVSWNSGALTSGVHTFPAVLQSSGLYSLSSVV
TVPSSSLGTQTYICNVNHKPSNTKVDKKVEPKC

SEQ ID NO: 16
DIQMTQSPSSSVAPGKTARIPCGGNNIGSKSVHWYQQKPGQAPVLVIY
YDSDRPSGIPERFSGSNSGNTATLTISRVEAGDEADYYCQVWDRSSDL
VVFGGGTKLTVLGQPKAAPSVTLFPPSSEELQANKATLVCLISDFYPG
AVTVAWKADSSPVKAGVETTTPSKQSNNKYAASSYLSLTPEQWKSHRS
YSCQVTHEGSTVEKTVAPTESS

Nucleic acid or amino acid sequence "identity," as described herein, can be determined by comparing a nucleic acid or amino acid sequence of interest to a reference nucleic acid or amino acid sequence. The percent identity is the number of nucleotides or amino acid residues that are the same (e.g., that are identical) as between the sequence of interest and the reference sequence divided by the length of the longest sequence (e.g., the length of either the sequence of interest or the reference sequence, whichever is longer). A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FAS™, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA*, 106(10): 3770-3775 (2009), Durbin et al., eds., *Biological Sequence Analysis: Probabilistic Models of Proteins and Nucleic Acids*, Cambridge University Press, Cambridge, UK (2009), Soding, *Bioinformatics,* 21(7): 951-960 (2005), Altschul et al., *Nucleic Acids Res.,* 25(17): 3389-3402 (1997), and Gusfield, *Algorithms on Strings, Trees and Sequences,* Cambridge University Press, Cambridge UK (1997)).

One or more amino acids of the aforementioned antibody or antigen fragment thereof can be replaced or substituted with a different amino acid. An amino acid "replacement" or "substitution" refers to the replacement of one amino acid at a given position or residue by another amino acid at the same position or residue within a polypeptide sequence.

In addition, one or more amino acids can be inserted into the antibody or antigen-binding fragment thereof (e.g., insertion into the heavy and/or light chain variable region amino acid sequence). Any number of any suitable amino acids can be inserted into the amino acid sequence of the antibody or antigen-binding fragment thereof. In this respect, at least one amino acid (e.g., 2 or more, 5 or more, or 10 or more amino acids), but not more than 20 amino acids (e.g., 18 or less, 15 or less, or 12 or less amino acids), can be inserted into the amino acid sequence of the antibody or antigen-binding fragment thereof. For example, 1-10 amino acids (e.g., 1, 2, 3, 4, 5, 6, 7, 8, 9, or 10 amino acids) may be inserted into the amino acid sequence of the antibody or antigen-binding fragment thereof. In this respect, the amino acid(s) can be inserted into antibody or antigen-binding fragment thereof in any suitable location. Preferably, the amino acid(s) are inserted into a CDR (e.g., CDR1, CDR2, or CDR3) of the antibody or antigen-binding fragment thereof.

The antibody or antigen-binding fragment thereof employed in the inventive method is not limited to a polypeptide comprising the specific amino acid sequences described herein. Indeed, the antibody or antigen-binding fragment thereof can comprise any heavy chain polypeptide or light chain polypeptide that competes with the inventive antibody or antigen-binding fragment thereof for binding to tenofovir or a tenofovir derivative. Antibody competition can be assayed using routine peptide competition assays such as, for example, ELISA, Western blot, or immunohistochemistry methods (see, e.g., U.S. Pat. Nos. 4,828,981 and 8,568,992; and Braitbard et al., *Proteome Sci.,* 4: 12 (2006)).

Antibodies may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, and the like. Although it is possible to express the antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies include Chinese Hamster Ovary (CHO cells) (including dhfr-CHO cells, described in Urlaub and Chasin, *Proc. Natl. Acad. Sci. USA,* 77: 4216-4220 (1980), used with a DHFR selectable marker, e.g., as described in Kaufman and Sharp, *J. Mol. Biol.,* 159: 601-621 (1982), NSO myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. In some aspects, the antibodies can be purified in CHO and/or HEK cells using routine techniques known in the art.

Host cells can also be used to produce functional antibody fragments, such as Fab fragments or scFv molecules. It will be understood that variations on the above procedure may be performed. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies.

In a preferred system for recombinant expression of an antibody, or antigen-binding portion thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the disclosure provides a method of synthesizing a recombinant antibody by culturing a host cell in a suitable culture medium until a recombinant antibody is synthesized. The method can further comprise isolating the recombinant antibody from the culture medium.

A humanized antibody may be an antibody or a variant, derivative, analog, or fragment or portion thereof which specifically binds to an antigen of interest and which comprises a framework (FR) region having substantially the amino acid sequence of a human antibody and a complementary determining region (CDR) having substantially the amino acid sequence of a non-human antibody. The humanized antibody may be from a non-human species antibody that binds the desired antigen having one or more complementarity determining regions (CDRs) from the non-human species and framework regions from a human immunoglobulin molecule.

As used herein, the term "substantially" in the context of a CDR refers to a CDR having an amino acid sequence at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (e.g., donor antibody) and all or substantially all of the framework regions are those of a human immunoglobulin consensus sequence. According to one aspect, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or of a heavy chain.

The humanized antibody can be selected from any class of immunoglobulins, including IgM, IgG, IgD, IgA and IgE, and any isotype, including without limitation IgG1, IgG2, IgG3, and IgG4. The humanized antibody may comprise sequences from more than one class or isotype, and particular constant domains may be selected to optimize desired effector functions using techniques well-known in the art.

The framework (FR) and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, *From Genes to Clones* (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

The humanized antibody may be designed to minimize unwanted immunological response toward rodent anti-human antibodies, which limits the duration and effectiveness of therapeutic applications of those moieties in human recipients. The humanized antibody may have one or more amino acid residues introduced into it from a source that is non-human. These non-human residues are often referred to as "import" residues, which are typically taken from a variable domain. Humanization may be performed by substituting hypervariable region sequences for the corresponding sequences of a human antibody. Accordingly, such "humanized" antibodies are chimeric antibodies wherein substantially less than an intact human variable domain has been substituted by the corresponding sequence from a non-human species. For example, see U.S. Pat. No. 4,816, 567, the contents of which are herein incorporated by reference. The humanized antibody may be a human antibody in which some hypervariable region residues, and possibly some FR residues are substituted by residues from analogous sites in rodent antibodies. Humanization or engineering of antibodies of the present disclosure can be performed using any known method, such as but not limited to those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

The humanized antibody may retain high affinity for SARS-CoV-2 antigens and other favorable biological properties. The humanized antibody may be prepared by a process of analysis of the parental sequences and various conceptual humanized products using three-dimensional models of the parental and humanized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind its antigen. In this way, framework residues can be selected and combined from the recipient and import sequences so that the desired antibody characteristics, such as increased affinity for SARS-CoV-2, is achieved. In general, the hypervariable region residues may be directly and most substantially involved in influencing antigen binding.

As an alternative to humanization, human antibodies (also referred to herein as "fully human antibodies") can be generated. For example, it is possible to isolate human antibodies from libraries via PROfusion and/or yeast related technologies. It is also possible to produce transgenic animals (e.g., mice that are capable, upon immunization, of producing a full repertoire of human antibodies in the absence of endogenous immunoglobulin production. For example, the homozygous deletion of the antibody heavy-chain joining region (JO gene in chimeric and germ-line mutant mice results in complete inhibition of endogenous antibody production. Transfer of the human germ-line immunoglobulin gene array in such germ-line mutant mice will result in the production of human antibodies upon antigen challenge. The humanized or fully human antibodies may be prepared according to the methods described in U.S. Pat. Nos. 5,770,429; 5,833,985; 5,837,243; 5,922,845; 6,017,517; 6,096,311; 6,111,166; 6,270,765; 6,303,755; 6,365,116; 6,410,690; 6,682,928; and 6,984,720, the contents each of which are herein incorporated by reference.

2. METHODS

The disclosed methods comprise contacting a sample obtained from a subject with a first antibody or antigen-binding fragment thereof that comprises a detectable label and specifically binds to a protein from the SARS-CoV-2 virus, or a fragment or epitope thereof, as described herein, under conditions which allow binding of protein from the SARS-CoV-2 virus, or a fragment or epitope thereof, if present in the sample, to the first antibody or antigen-binding fragment thereof to form a first complex. In some embodiments, the protein from the SARS-CoV-2 virus is a viral genome packaging protein (e.g., nucleocapsid (N) protein, e.g., as provided by UniProtKB Accession Number P0DTC9).

The sample may undergo one or more processing steps prior to contacting with the first antibody or antibody-binding fragment thereof. In some embodiments, such processing steps include addition of one or more preservatives or stabilizers to facilitate storage or shipment of the sample from a location of collection to a location of testing. In some embodiments, such processing steps include a purification step (e.g., using a filter, centrifugation, etc.) that removes one or more components from the sample to enrich the sample for an analyte of interest.

The first antibody or antigen-binding fragment thereof may be contacted with the sample using any suitable method known in the art. The term "contacting," as used herein, refers to any type of combining action which brings an antibody, particular an antibody immobilized on a solid support, into sufficiently close proximity with an analyte of interest in a sample (e.g., a protein from the SARS-CoV-2 virus) such that a binding interaction will occur if the analyte of interest specific for the antibody is present in the sample. Contacting may be achieved in a variety of different ways, including directly combining the sample with the antibody or antigen-binding fragment thereof, or exposing the sample to a solid support comprising the antibody or antigen-binding fragment thereof by introducing the solid support in close proximity to the sample. The contacting may be repeated as many times as necessary or for an amount of time necessary such that the binding interactions occurs.

The methods described herein desirably are performed using an immunoassay. The term "immunoassay," as used herein, refers to a biochemical test that measures the presence or concentration of a macromolecule or a small molecule in a solution through the use of an antibody or an antigen. Any suitable immunoassay may be used, and a wide variety of immunoassay types, configurations, and formats are known in the art and within the scope of the present disclosure. Suitable types of immunoassays include, but are not limited to, enzyme-linked immunosorbent assay (ELISA), lateral flow assay, competitive inhibition immunoassay (e.g., forward and reverse), radioimmunoassay (RIA), fluoroimmunoassay (FIA), chemiluminescent immunoassay (CLIA), counting immunoassay (CIA), enzyme multiplied immunoassay technique (EMIT), one-step antibody detection assay, homogeneous assay, heterogeneous assay, capture on the fly assay, single molecule detection assay, etc. Such methods are disclosed in, for example, U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; 5,480,792; 11,022,598 International Patent Application Publication WO 2016/161400; and Adamczyk et al., *Anal. Chico. Acta,* 579(1): 61-67 (2006).

The immunoassay format may be "direct" or "indirect" "sandwich." Sandwich formats involve the use of capture and detection antigens to immobilize and detect an antigen in a sample. Specifically, the surface of a solid support (e.g., ELISA plate, bead, etc.) is coated with a capture antibody or antigen-binding fragment thereof, which capture antibody binds to and immobilizes a target antigen present in a sample applied thereto. A detection antibody is then added or contacted to the complex. The detection antibody can be directly labeled with an antibody ("direct sandwich immunoassay") to allow for detection and quantification of the antigen. Alternatively, if the detection antibody is unlabeled, a secondary enzyme-conjugated detection antibody may be used ("indirect sandwich assay").

Thus, the disclosed method may further comprise contacting the sample with a conjugate comprising a second antibody, wherein second antibody, or antigen-binding fragment thereof, portion of the conjugate specifically binds to a target antigen (e.g., a protein from the SARS-CoV-2 virus, or a fragment or epitope thereof), which results in the linkage of the conjugate to the captured analyte and formation of an immunosandwich (also referred to herein as an "immunosandwich complex"). It will be appreciated that, in sandwich immunoassay formats, the first antibody and the second antibody recognize two different non-overlapping epitopes on a target analyte/antigen.

In certain embodiments, the first antibody, or antigen-binding fragment thereof, may be attached to, or immobilized on, a solid support. The terms "solid phase" and "solid support" are used interchangeably herein and refer to any material that can be used to attach and/or attract and immobilize one or more antibodies. Any solid support known in the art can be used in the methods described herein. Examples of suitable solid supports include electrodes, test tubes, beads, microparticles, nanoparticles, wells of micro- or multi-well plates, gels, colloids, biological cells, sheets, strips, and chips.

In one embodiment, a solid support desirably comprises a plurality (e.g., 2 or more, 50 or more, 100 or more, 1,000 or more, or 5,000 or more) of antibodies, or antigen-binding fragments thereof, immobilized on the surface thereof which bind to a protein from the SARS-CoV-2 virus, or a fragment or epitope thereof. The term "immobilized," as used herein, refers to a stable association of a binding member with a surface of a solid support. Following a sufficient incubation time between the solid support and the sample, as discussed herein, a protein from the SARS-CoV-2 virus, or a fragment or epitope thereof, if present in the sample, desirably is captured on the surface of the solid support via the immobilized antibody.

An antibody or antibody fragment may be attached to a solid support via a linkage, which may comprise any moiety, functionalization, or modification of the support and/or antibody that facilitates the attachment of the antibody to the support. The linkage between the antibody and the support may include one or more chemical or physical bonds (e.g., non-specific attachment via van der Waals forces, hydrogen bonding, electrostatic interactions, hydrophobic/hydrophilic interactions, etc.) and/or chemical spacers providing such bond(s). Any number of techniques may be used to attach an antibody to a wide variety of solid supports (see, e.g., U.S. Pat. No. 5,620,850; and Heller, *Acc. Chem. Res.,* 23: 128 (1990)).

In some embodiments, the binding affinity between protein from the SARS-CoV-2 virus, or a fragment or epitope thereof, and the first or second antibody or antibody fragments should be sufficient to remain bound under the conditions of the assay, including wash steps to remove molecules or particles that are non-specifically bound. Contact is desirably maintained (e.g., incubated) for a sufficient period of time to allow for the binding interaction between the protein from the SARS-CoV-2 virus, or a fragment or epitope thereof, and the first or second antibodies or antibody fragments to occur. In addition, the incubating may be in a binding buffer that facilitates the specific binding interaction, such as, for example, albumin (e.g., BSA), non-ionic detergents (Tween-20, Triton X-100), and/or protease inhibitors (e.g., PMSF). The binding affinity and/or specificity of the first or second antibodies or antibody fragments may be manipulated or altered in the assay by varying the binding buffer.

Any unbound antibody, antibody fragment, or component of the conjugate may be separated from an immunosandwich by any suitable means such as, for example, droplet actuation, electrophoresis, electrowetting, dielectrophoresis, electrostatic actuation, electric field mediated, electrode mediated, capillary force, chromatography, centrifugation, aspiration, or surface acoustic wave (SAW)-based washing methods.

The method further comprises assessing the presence of a signal from a detectable label conjugated to the second antibody, wherein the presence of a signal from the detectable label indicates the presence of a protein from the SARS-CoV-2 virus, or a fragment or epitope thereof in the sample.

Suitable detectable labels include various enzymes, prosthetic groups, fluorescent materials, luminescent materials, and radioactive materials (see, e.g., Zola, Monoclonal Antibodies: A Manual of Techniques, CRC Press, Inc. (1987)). For example, the detectable label can be a radioisotope (e.g., $^{3}H$, $^{14}C$, $^{32}P$, $^{35}S$, or $^{125}I$), a fluorescent or chemiluminescent compound (e.g., fluorescein isothiocyanate, rhodamine, or luciferin), or an enzyme (e.g., alkaline phosphatase, beta-galactosidase, or horseradish peroxidase). Any method known in the art for separately conjugating an antibody to a detectable label may be employed in the context of the disclosure (see, e.g., Hunter et al., *Nature*, 144: 945 (1962); David et al., *Biochemistry*, 13: 1014 (1974); Pain et al., *J. Immunol. Meth.*, 40: 219 (1981); and Nygren, *J. Histochem. and Cytochem.*, 30: 407 (1982)). Signal generated from a detectable label attached to an antibody can be measured based on its spectroscopic properties.

It will be appreciated that different conformations of the antigen capture and immunosandwich formation methods described above are within the scope of the present disclosure. Indeed, the various components of the solid support, conjugates, and detectable labels described above may be arranged or utilized in any suitable combination, conformation, or format. For example, the disclosed methods may be performed in one-step, delayed one-step, or two-step format with either the sample being incubated with the first antibody followed by the second or vice versa. Assay reagents (e.g., microparticles, conjugates, fluorophores, etc.) may be pre-mixed or added sequentially as appropriate.

In one embodiment, a lateral flow assay is used. Lateral flow assays provide technologies for qualitatively detecting and/or quantitatively measuring analytes in a short time using antigen-antibody interaction (e.g., using immunochromatography). These tests typically use an assay device in the form of an assay test strip or a device in which the assay strip is mounted inside a plastic case. See, e.g., Int'l Pat. App. Pub. No. WO2011102563A1; U.S. Pat. No. 8,828,739, each of which is incorporated herein by reference.

Lateral flow assays are generally provided in a device comprising a lateral flow test strip (e.g., nitrocellulose or filter paper), a sample application area (e.g., sample pad), a test results area (e.g., a test line), an optional control results area (e.g., a control line), and an analyte-specific binding reagent that is bound to a detectable label (e.g., a colored particle or an enzyme detection system). See, e.g., U.S. Pat. Nos. 6,485,982; 6,187,598; 5,622,871; 6,565,808; 6,809,687; and 10,717,082, each of which is incorporated herein by reference. In some embodiments, the technology relates to a test device comprising a reagent-impregnated test strips to provide a specific binding assay, e.g., an immunoassay.

In some embodiments, the disclosure relates to lateral flow devices that are suitable for use in the home, clinic, or hospital, and that are intended to give an analytical result that is rapid with minimum degree of skill and involvement from the user. In some embodiments, use of the devices described herein involves methods in which a user performs a sequence of operations to provide an observable test result.

In some embodiments, the lateral flow devices comprise: a first antibody which specifically binds to a protein from the SARS-CoV-2 virus, or a fragment thereof, and a second antibody which specifically binds to a protein from the SARS-CoV-2 virus, or a fragment thereof. Description of the antibodies provided above are relevant to the lateral flow devices described herein. In some embodiments, the test line of the device comprises the first antibody. In some embodiments, the sample pad comprises the second antibody.

In some embodiments, the sample is applied to one portion of a test strip and is allowed to permeate through the strip material, usually with the aid of an eluting solvent such as water and/or a suitable extraction buffer (e.g., optionally comprising a detergent). In so doing, the sample progresses into or through a detection zone in the test strip wherein a specific binding reagent (e.g., an antibody) for an analyte (e.g., a protein from the SARS-CoV-2 virus, or a fragment or epitope thereof) suspected of being in the sample is immobilized. Analyte present in the sample can therefore become bound within the detection zone. The extent to which the analyte becomes bound in that zone can be determined with the aid of labelled reagents that can also be incorporated in the test strip or applied thereto subsequently.

In some embodiments, the analytical test device comprises a hollow casing constructed of moisture-impervious solid material containing a dry porous carrier that communicates directly or indirectly with the exterior of the casing such that a liquid test sample can be applied to the porous carrier. In some embodiments, the device also comprises a labelled specific binding reagent for an analyte and the labelled specific binding reagent is freely mobile within the porous carrier when in the moist state. In some embodiments, the device comprises unlabeled specific binding reagent for the same analyte and the unlabeled reagent is permanently immobilized in a detection zone on the carrier material and is therefore not mobile in the moist state. The relative positioning of the labelled reagent and detection zone being such that liquid sample applied to the device can pick up labelled reagent and thereafter permeate into the detection zone and the device provides the extent (if any) to which the labelled reagent becomes in the detection zone to be observed.

In some embodiments, the device comprises a porous solid phase material carrying in a first zone a labelled reagent that is retained in the first zone while the porous material is in the dry state but is free to migrate through the porous material when the porous material is moistened, for example, by the application of an aqueous liquid sample suspected of containing the analyte. In some embodiments, the porous material comprises in a second zone, which is spatially distinct from the first zone, an unlabeled specific binding reagent having specificity for the analyte and which is capable of participating with the labelled reagent in either a "sandwich" or a "competition" reaction. The unlabeled specific binding reagent is firmly immobilized on the porous material such that it is not free to migrate when the porous material is in the moist state.

In some embodiments, a device as described herein is contacted with an aqueous liquid sample suspected of containing the analyte, such that the sample permeates by capillary action through the porous solid phase material via the first zone into the second zone and the labelled reagent migrates therewith from the first zone to the second zone, the presence of analyte in the sample being determined by observing the extent (if any) to which the labelled reagent becomes bound in the second zone.

In some embodiments, the labelled reagent is a specific binding partner for the analyte. The labelled reagent, the analyte (if present), and the immobilized unlabeled specific binding reagent cooperate together in a "sandwich" reaction. This results in the labelled reagent being bound in the second zone if analyte is present in the sample. In a sandwich format, the two binding reagents have specificities for different epitopes on the analyte. In some embodiments, the first antibody is immobilized. In some embodiments, the second antibody comprises a detectable label.

In some embodiments, the test strip (e.g., the carrier material) comprises nitrocellulose. This has considerable advantage over some other strip materials, such as paper, because it has a natural ability to bind proteins without requiring prior sensitization. Specific binding reagents, such as immunoglobulins, can be applied directly to nitrocellulose and immobilized thereon. No chemical treatment is required that might interfere with the essential specific binding activity of the reagent. Unused binding sites on the nitrocellulose can thereafter be blocked using simple materials, such as polyvinylalcohol. Moreover, nitrocellulose is readily available in a range of pore sizes and this facilitates the selection of a carrier material to suit particularly requirements such as sample flow rate.

In some embodiments, the porous solid phase material is linked to a porous receiving member to which the liquid sample can be applied and from which the sample can permeate into the porous solid phase material. In some embodiments, the porous solid phase material is contained within a moisture-impermeable casing or housing and the porous receiving member, with which the porous solid phase material is linked, extends out of the housing and can act as a means for permitting a liquid sample to enter the housing and permeate the porous solid phase material. The housing should be provided with means, e.g., appropriately placed apertures, that enable the second zone of the porous solid phase material (carrying the immobilized unlabeled specific binding reagent) to be observable from outside the housing so that the result of the assay can be observed. If desired, the housing may also be provided with further means which enable a further zone of the porous solid phase material to be observed from outside the housing and which further zone one incorporates control reagents which enable an indication to be given as to whether the assay procedure has been completed. In some embodiments, the housing is provided with a removable cap or shroud that can protect the protruding porous receiving member during storage before use. If desired, the cap or shroud can be replaced over the protruding porous receiving member, after sample application, while the assay procedure is being performed. optionally, the labelled reagent can be incorporated elsewhere within the device, e.g., in the bibulous sample collection member, but his is not preferred.

In some embodiments, devices are provided as kits suitable for use in a hospital, clinic, or home. In some embodiments, kits comprise a plurality (e.g., two) of devices individually wrapped in moisture impervious wrapping and packaged together with appropriate instructions to the user.

In some embodiments, the device comprises an optional "control zone". If present, the "control" zone can be designed to convey an unrelated signal to the user that the device has worked. For example, the control zone can be loaded with an antibody (e.g., goat anti-rabbit IgG) that will bind to a labelled antibody from the first zone, e.g., a labeled rabbit IgG, to confirm that the sample has permeated the test strip. In some embodiments, the first zone comprises an antigen and/or antibody that is unrelated to the analyte and that is specifically captured at the control zone. In some embodiments, the control zone can contain an anhydrous reagent that, when moistened, produces a color change or color formation, e.g., anhydrous copper sulphate which will turn blue when moistened by an aqueous sample. As a further alternative, a control zone could contain immobilized analyte that reacts with excess labelled reagent from the first zone. As the purpose of the control zone is to indicate to the user that the test has been completed, the control zone should be located downstream from the second zone in which the desired test result is recorded. A positive control indicator therefore tells the user that the sample has permeated the required distance through the test device.

Ideally, the result of the assay should be discernable by eye and to facilitate this, it is necessary for the direct label to become concentrated in the detection zone. In some embodiments, the detectable label is a direct label, e.g., an entity that, in its natural state, is readily visible either to the naked eye or with the aid of an optical filter and/or applied stimulation, e.g., UV light to promote fluorescence. For example, minute colored particles, such as dye sols, metallic sols (e.g., gold), and colored latex particles, are very suitable. Concentration of the label into a small zone or volume (e.g., test line) gives rise to a readily detectable signal, e.g., a strongly-colored area. This can be evaluated by eye, or by instruments if desired.

In some embodiments, the technology comprises use of an indirect label. Indirect labels, such as enzymes, e.g., alkaline phosphatase and horseradish peroxidase, can be used but these usually require the addition of one or more developing reagents such as substrates before a visible signal can be detected. Such additional reagents can be incorporated in the porous solid phase material or in the sample receiving member, if present, such that they dissolve or disperse in the aqueous liquid sample. Alternatively, the developing reagents can be added to the sample before contact with the porous material or the porous material can be exposed to the developing reagents after the binding reaction has taken place.

In some embodiments, the flow of sample continues beyond the detection zone and sufficient sample is applied to the porous material so that this may occur and that any excess labelled reagent from the first zone that does not participate in any binding reaction in the second zone is flushed away from the detection zone by this continuing flow. If desired, an absorbent "sink" can be provided at the distal end of the carrier material. The absorbent sink may comprise of, for example, Whatman 3 MM chromatography paper, and should provide sufficient absorptive capacity to allow any unbound conjugate to wash out of the detection zone. As an alternative to such a sink it can be sufficient to have a length of porous solid phase material which extends beyond the detection zone.

In some embodiments, the carrier material is in the form of a strip or sheet to which the reagents are applied in spatially distinct zones and the liquid sample is allowed to permeate through the sheet or strip from one side or end to another.

In some embodiments, the material comprising the porous solid phase is nitrocellulose. This has the advantage that the antibody in the second zone can be immobilized firmly without prior chemical treatment. If the porous solid phase material comprises paper, for example, the immobilization of the antibody in the second zone needs to be performed by chemical coupling using, for example, CNBr, carbonyldiimidazole, or tresyl chloride.

Following the application of the antibody to the detection zone, the remainder of the porous solid phase material is treated to block any remaining binding sites elsewhere. Blocking can be achieved by treatment with protein (e.g., bovine serum albumin or milk protein) or with polyvinylalcohol or ethanolamine, or any combination of these agents, for example. The labelled reagent for the first zone can then be dispensed onto the dry carrier and will become mobile in the carrier when in the moist state. Between each of these various process steps (sensitization, application of unlabeled reagent, blocking and application of the labelled reagent), the porous solid phase material is dried.

The disclosed methods may comprise quality control components. "Quality control components" in the context of immunoassays and kits described herein, include, but are not limited to, calibrators, controls, and sensitivity panels. A "calibrator" or "standard" can be used (e.g., one or more, such as a plurality) in order to establish calibration (standard) curves for interpolation of the concentration of an analyte, such as an antigen. Alternatively, a single calibrator, which is near a reference level or control level (e.g., "low", "medium", or "high" levels), can be used. Multiple calibrators (e.g., more than one calibrator or a varying amounts of calibrator(s)) can be used in conjunction to comprise a "sensitivity panel." The calibrator is optionally part of a series of calibrators in which each of the calibrators differs from the other calibrators in the series, such as, for example, by concentration or detection method (e.g., colorimetric or fluorescent detection).

The disclosed methods may further comprise detecting one or more pathogens, or antigens thereof, in addition to SARS-CoV-2. The pathogen can be any infectious organism that causes an infectious disease of interest, or that can cause disease symptoms for which a diagnostic differential is necessary for appropriate therapy. Infectious organisms of interest include bacteria (including, but not limited to, *Escherichia* species, *Streptococcus* species, *Haemophilus* species, *Staphylococcus* species, and *Neisseria* species), viruses (including, but not limited to, Adenovirus, Enterovirus, Echovirus, Human herpesvirus, Mumps virus Ag, Influenza, Parainfluenza, Respiratory syncytial virus (RSV), other human coronaviruses, Rhinovirus, human metapneumovirus), or eukaryotic pathogens (including fungi and protozoans). In some embodiments, the methods further comprise detecting Influenza, Rhinovirus, RSV, and/or Adenovirus.

The detecting of other pathogens may use the same type of methods, e.g., immunoassays as described above, as used for detection of SARS-CoV-2 antigens. Alternatively, the detecting of other pathogens may use a non-immunoassay of detection, including but not limited to, nucleic acid detection (e.g., microarray), nucleic acid amplification (e.g., RT-PCR) and/or sequencing (e.g., next generation sequencing), immunofluorescence assays, serological assays, and cell culture based detection.

The detecting of other pathogens may be done concurrently, before, or after the detection of SARS-Cov-2 antigens. For example, if the method of detecting the other pathogens is the same type of immunoassay, the sample may be incubated with the detection reagents for the other pathogens at the same time as those for detection of SARS-Cov-2 antigens (e.g., a single sample pad for multiple test strips in a lateral flow assay).

3. KITS AND INSTRUMENTATION

Also provided herein are kits for performing the above-described methods. Instructions included in the kit may be affixed to packaging material or may be included as a package insert. The instructions may be written or printed materials but are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), etc. As used herein, the term "instructions" may include the address of an internet site that provides the instructions.

The kit may include a lateral flow device as described herein. In some embodiments, the lateral flow device is in a sealed package (e.g., wrapped in moisture impervious wrapping). The lateral flow device may be disposable. In some embodiments, devices are provided as kits suitable for use in a hospital, clinic, or home. In some embodiments, kits comprise a plurality (e.g., two) of devices individually wrapped in moisture impervious wrapping and packaged together with appropriate instructions to the user.

The kit may include a sample container. The sample container may be a cuvette. The sample holder may be a cartridge that includes a microfluidics module. The sample holder may be an ELISA plate. The sample container may include one or more reagents useful for practicing the methods disclosed herein (e.g., binding buffer and antibodies). The sample holder may also include other material(s) that may be desirable from a user standpoint, such as buffer(s), a diluent(s), a standard(s) (e.g., calibrators and controls), and/or any other material useful in sample processing, washing, or conducting any other step of the assay.

The kit may further comprise reference standards for detecting a protein from the SARS-CoV-2 virus, or a fragment thereof, in the sample. The reference standards may be employed to establish standard curves for interpolation and/or extrapolation of the protein from the SARS-CoV-2 virus, or a fragment thereof, concentrations. The kit may include reference standards that vary in terms of concentration level. For example, the kit may include one or more reference standards with either a high concentration level, a medium concentration level, or a low concentration level. In terms of ranges of concentrations for the reference standard, this can be optimized per the assay.

The kit may also include quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics and are useful indicators of the integrity of the kit reagents and the standardization of assays.

The kit may also optionally include other reagents required to detect additional pathogens in the sample, and any reference standards or quality control components thereof.

The kit may also optionally include other reagents required to conduct an assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents or extraction buffers), also can be included in the kit. The kit may additionally include one or more other controls. One or more of the components of the kit can be lyophilized, in which case the kit can further comprise reagents suitable for the reconstitution of the lyophilized components. One or more of the components may be in liquid form.

The various components of the kit optionally are provided in suitable containers as necessary. The kit further can include containers for holding or storing a sample (e.g., a container or cartridge for a sample). Where appropriate, the kit optionally can contain reaction vessels, mixing vessels, and other components that facilitate the preparation of reagents or the test sample. The kit can also include one or more sample collection/acquisition instruments for assisting with obtaining a test sample (e.g., microsampling devices, micro-needles, or other minimally invasive pain-free blood collection methods; blood collection tube(s); lancets; capillary blood collection tubes; other single fingertip-prick blood collection methods; buccal swabs, nasal/throat swabs; 16-gauge or other size needle, surgical knife or laser (e.g., particularly hand-held), syringes, sterile container, or canula, for obtaining, storing, or aspirating tissue samples).

The concepts, kits, and methods as described herein can be implemented on any system or instrument, including any manual, automated, or semi-automated system for conducting immunoassays. In certain embodiments, the assays, kits, and kit components described herein can be implemented in a hospital, home, or clinic.

In certain embodiments, the assays, kits, and kit components described herein can be implemented on a high-throughput immunoassay laboratory systems, such as, for example, the Abbott™ ARCHITECT™ (Abbott Laboratories) immunoassay analyzer. Such devices and its components are described in, for example, U.S. Pat. Nos. 5,468,646; 5,543,524; 5,545,739; 5,565,570; 5,669,819; and 5,783,699.

In certain embodiments, the assays, kits, and kit components described herein can be implemented on electrochemical or other hand-held or point-of-care assay systems, such as, for example, the Abbott Point of Care (I-STAT®, Abbott Laboratories) electrochemical assay system that performs sandwich assays and Axis-Shield POC AS. Immunosensors and their methods of manufacture and operation in single-use test devices are described in, for example, U.S. Pat. Nos. 5,063,081; 7,419,821; 7,682,833; and 7,723,099 and U.S. Patent Application Publication No. 2004/0018577.

4. EXAMPLES

Example 1

Lateral Flow Assay

An exemplary lateral flow assay for detecting SARS-CoV-2 is provided that makes use of a sandwich-type assay. In particular, the device comprises a first zone (e.g., a reagent zone) comprising a labeled antibody that is specific for a protein from the SARS-CoV-2 virus, or a fragment thereof, e.g., a monoclonal antibody labeled with a detectable label. The device comprises a second antibody specific for a different epitope from a protein from the SARS-CoV-2 virus, or a fragment thereof, immobilized at a second zone (e.g., a detection zone). A positive test is indicated by the appearance of a visible line at the detection zone (e.g., at a test line).

Initial testing of the device was performed on heat inactivated SARS-CoV-2 virus diluted onto a foam swab which was applied to the reagent zone. The LOD was found to be 22.5 fifty-percent-tissue-culture-infective-dose ($TCID_{50}$) ($TCID_{50}$)/test dilution or 1125 $TCID_{50}$/mL.

No cross-reactivity was observed with a number of other viruses tested, including Adenovirus (Type 1, Type 5 and Type 7), Enterovirus (EV68 and D68), Echovirus (Type 1 and Type 2), Human herpesvirus (Type 1 and Type 2), Mumps virus Ag, Influenza Virus A (H1N1 Strain (A/Virginia/ATCC1/2009), H1N1 Strain (A/WS/33), and H3N2 Strain (A/Hongkong/8/68)), Influenza B (Strain (B/Lee/40)), Parainfluenza (Type 1, Type 2, Type 3 and Type 4A), Respiratory syncytial virus or RSV (Type A and Type B), Human coronaviruses (HKU1, NL63, OC43 and 229E), Rhinovirus (Type A16), MERs-CoV, and Human metapneumovirus (16Type A1). In addition, co-infection with non-SARS-CoV-2 viruses (Influenza A, Rhinovirus, RSV, or Adenovirus) did not affect detection of the SARS CoV-2 near the limit of detection.

However, cross-reactivity was observed to human SARS-coronavirus when 25 ng/mL to 25 µg/mL human SARS-coronavirus nucleoprotein were used, likely due to the 79.6% similarity between the genomes or SARS-CoV and SARS-CoV-2. Samples comprising 2.5 ng/mL human SARS-coronavirus nucleoprotein did not result in a cross reaction.

No cross-reactivity was observed with other organisms, including Candida albicans, Chlamydia pneumoniae, Streptococcus pyogenes (Group A 19615), Staphylococcus aureus, Staphylococcus saprophyticus, Neisseria sp. (Neisseria lactamica), Escherichia coli, Staphylococcus haemolyticus, Streptococcus salivarius, Hemophilus parahaemolyticus, Proteus vulgaris, Moraxella catarrhalis, Klebsiella pneumoniae, Fusobacterium necrophorum, and Mycobacterium tuberculosis. In addition, no cross-reactivity was observed with a polled human nasal wash sample.

Testing was also performed with the inclusion of a variety of known interfering substances, including endogenous substances such as mucin, hemoglobin, triglycerides, icteric (bilirubin), rheumatoid factor, anti-nuclear antibody, pregnancy, and whole blood, as well as, expectorants, such as guaiacol glyceryl ether; bronchodilators, such as albuterol and ephedrine; anti-histamines, such as chlorpheniramine and diphenhydramine; nasal decongestants, such as phenylephrine hydrochloride and oxymetazoline hydrochloride; anti-viral drugs, such as ribavirin, oseltamivir, and zanamivir; antibiotic drugs, such as amoxicillin; common drugs, such as acetylsalicylic acid and ibuprofen; anti-hypertensive drugs, such as chlorothiazide and indapamide; anti-diabetic drugs, such as glimepiride (sulfonylureas) and indapamide; and putative COVID-19 drugs, such as ivermectin, lopinavir, ritonavir, and chloroquine phosphate. Solutions of the interfering substances were spiked onto a foam swab or sample repository and the testing was completed as described above. No interference was observed at the concentrations tested.

Example 2

Lateral Flow Assay Kit

An exemplary lateral flow assay kit includes at least one or all of: an extraction buffer; a lateral flow device; a positive control swab comprising recombinant SARS-CoV-2 N protein in 1× XTBE and 1% BSA solution; a nitrocellulose test strip with a test line and a control line; a patient swab (e.g., foam tipped applicator); and at least one or both of the first and second antibodies or fragments thereof, separately or within the lateral flow device. The lateral flow device comprises test strip components including: a bridge pad (e.g., Ahlstrom 1281—Ahlstrom Filtration Inc., Mt. Holly Springs, Pa.), a conjugate pad (e.g., PN PK002123), a sample pad (e.g., Ahlstrom 1281—Ahlstrom Filtration Inc., Mt. Holly Springs, Pa.), an Abs pad (e.g., Ahlstrom 904—Ahlstrom Filtration Inc., Mt. Holly Springs, Pa.), and a housing. The extraction buffer comprises 200 mM Tricine, 1.2% NaCl, 0.75% Zwittergent, 0.5% Tween 20, and 0.0125% azide at pH 8.8. The test line was embedded or treated with a solution comprising: 2 mg/mL BSA-Fab, 1.5% Trehalose, 50 mM Tris, 0.1% azide and 0.02% Intrawhite (UV). The control line was embedded or treated with a solution comprising: 1 mg/mL Chicken IgY, 1% Trehalose, 50 mM Tris, 0.1% azide, and 0.05% FD&C blue dye.

The second, or conjugate antibody or fragment thereof, was provided with a resuspension buffer (e.g., 5 mM Borate, 0.1% Casein, 0.01% PEG Compound, and 0.01% azide at pH 7.4) and a drying buffer (e.g., 5 mM Borate, 2% Enzymatic Casein (N-Z Case), 0.1% Triton X-100, 2% Tween 20, 6% Sucrose, and 0.02% azide at pH 8). The second or conjugate antibody or fragment thereof may comprise SEQ ID NOs: 15 and 16 or a derivative thereof, and BSA-Free Donkey anti-chicken.

Example 3

Lateral Flow Assay Kit

An exemplary lateral flow device comprising the first and second antibodies as disclosed herein was tested using 243 nasopharyngeal specimens collected on individuals suspected of exposure to COVID-19 or presented COVID-19 symptoms in the last 7 days (60 PCR-positives and 183 PCR-negatives). The results show an overall percent agreement of 97.9% (Table 1).

TABLE 1

|  | PCR Test Result | | |
| --- | --- | --- | --- |
|  | Positive | Negative | Total |
| Positive | 56 | 1 | 57 |
| Negative | 4 | 182 | 186 |
| Total | 60 | 183 | 243 |
|  | Positive Percent Agreement 93.3% [83.8%; 98.2%] | Negative Percent Agreement 99.5% [97.0%; 100.0%] | Overall Percent Agreement 97.9% [95.3%; 99.3%] |

Example 4

Lateral Flow Assay Comparisons

Exemplary lateral flow devices were tested for clinical sensitivity and specificity against a reference method comprising RealTime PCR (RT-PCR) of SARS-CoV-2 in samples from nasal swabs of patients suspected of COVID-19 infection. One exemplary lateral flow device comprised full-length versions of the first and second antibodies described herein, whereas the second lateral flow device comprised Fab antibody fragments of the first and second antibodies. Two nasal swabs from each patient were collected; one for direct testing using the lateral flow assay and the other was placed in viral transfer media and chilled to 2-8° C. for subsequent RT-PCR analysis. The order of nasal swab collection was randomized.

The exemplary lateral flow device comprising full-length antibodies was found to have a percent positive agreement of approximately 68% for all samples, symptomatic patients only, when compared to RT-PCR analysis (Table 2). The percent positive agreement was approximately 90% when compared to culturable virus measurements (CT cutoff=23), although the percent negative agreement decreased slightly (Table 3). The majority of the patients (100) presented symptoms for less than 7 days and the results were similar to summary results for all patients as shown in Table 2. However, the small sample size of patients presenting symptoms for 8-10, 11-14, or greater than 15 days resulted in large 95% confidence intervals.

TABLE 2

| Lateral Flow | RT-PCR (All) | | | RT-PCR (symptomatic) | | | RT-PCR (asymptomatic) | | |
| --- | --- | --- | --- | --- | --- | --- | --- | --- | --- |
|  | POS | NEG | Total | POS | NEG | Total | POS | NEG | Total |
| Positive | 27 | 1 | 28 | 27 | 1 | 28 | 0 | 0 | . |
| Negative | 13 | 75 | 88 | 13 | 75 | 88 | 0 | 0 | . |
| Total | 40 | 76 | 116 | 40 | 76 | 116 | 0 | 0 | . |
| % Pos Agreement (95% CI) |  |  | 67.5 (50.9, 81.4) |  |  | 67.5 (50.9, 81.4) |  |  |  |
| % Neg Agreement (95% CI) |  |  | 98.7 (92.9, 100.0) |  |  | 98.7 (92.9, 100.0) |  |  |  |
| % Overall Agreement (95% CI) |  |  | 87.9 (80.6, 93.2) |  |  | 87.9 (80.6, 93.2) |  |  |  |

TABLE 3

|  | Culturable Virus (CT cutoff = 23) | | |
| --- | --- | --- | --- |
| Lateral Flow | POS | NEG | Total |
| Positive | 20 | 8 | 28 |
| Negative | 2 | 86 | 88 |
| Total | 22 | 94 | 116 |
| % Pos Agreement (95% CI) |  |  | 90.9 (70.8, 98.9) |
| % Neg Agreement (95% CI) |  |  | 91.5 (83.9, 96.3) |
| % Overall Agreement (95% CI) |  |  | 91.4 (84.7, 95.8) |

The exemplary lateral flow device comprising Fab antibody fragments resulted in noticeably higher percent positive agreement than the devices using full length-antibodies. The percent positive agreement of all patient samples (symptomatic and asymptomatic patients) was of approximately 90%; for symptomatic patients the percent positive agreement was 91.5% (Table 4). Similar results were found comparing the Fab lateral flow device to Culturable Virus (CT cutoff=23). Due to the low sample size, the percent positive agreement of asymptomatic patients had large error, as indicated in the 95% confidence intervals. (Table 4).

TABLE 4

| Lateral Flow | RT-PCR (All) | | | RT-PCR (symptomatic) | | | RT-PCR (asymptomatic) | | |
| --- | --- | --- | --- | --- | --- | --- | --- | --- | --- |
| | POS | NEG | Total | POS | NEG | Total | POS | NEG | Total |
| Positive | 44 | 2 | 46 | 43 | 2 | 45 | 1 | 0 | 1 |
| Negative | 5 | 81 | 86 | 4 | 77 | 81 | 1 | 4 | 5 |
| Total | 49 | 83 | 132 | 47 | 79 | 126 | 2 | 4 | 6 |
| % Pos Agreement (95% CI) | | | 89.8 (77.8, 96.6) | | | 91.5 (79.6, 97.6) | | | 50.0 (1.3, 98.7) |
| % Neg Agreement (95% CI) | | | 97.6 (91.6, 99.7) | | | 97.5 (91.2, 99.7) | | | 100.0 (39.8, 100.0) |
| % Overall Agreement (95% CI) | | | 94.7 (89.4, 97.8) | | | 95.2 (89.9, 98.2) | | | 83.3 (35.9, 99.6) |

The majority of the symptomatic patients (102/126) presented symptoms for less than 7 days. In those samples, the percent positive agreement and the overall agreement all increased to 97.1%, and 98.0%, respectively; percent negative agreement remained substantially the same. However, similar to the total asymptomatic patient numbers, the low sample size of symptomatic patients having symptoms for 8-10 days (5 patients), 11-14 day (13 patients) and greater than 15 days (6 patients) resulted in large amounts of error in the percent positive agreement measurements of 100.0% (29.2, 100.0), 62.5% (24.5, 91.5) and 100.0% (2.5, 100.0), respectively. As shown in Table 5, samples from symptomatic patients for 10 days or less resulted in percent overall agreement of approximately 98%.

TABLE 5

| Subjects with Symptom ≤10 Days | RT-PCR | | |
| --- | --- | --- | --- |
| Lateral Flow | POS | NEG | Total |
| Positive | 37 | 1 | 38 |
| Negative | 1 | 68 | 69 |
| Total | 38 | 69 | 107 |
| % Pos Agreement (95% CI) | | | 97.4 (86.2, 99.9) |
| % Neg Agreement (95% CI) | | | 98.6 (92.2, 100.0) |
| % Overall Agreement (95% CI) | | | 98.1 (93.4, 99.8) |

Using Fab antibody fragments in place of full-length antibodies in the lateral flow device increased the percent positive agreement from approximately 68% to approximately 90% and the percent overall agreement from approximately 88% to approximately 95% for all patient samples tested and increased the percent positive, percent negative and percent overall agreement for samples from patients having symptoms for 10 days or less.

Example 5

Lateral Flow Assay

Additional testing using a lateral flow device comprising full-length versions of the first and second antibodies, as described herein, was performed on heat inactivated SARS-CoV-2 isolated from a confirmed positive patient. The LOD was found to be 79 fifty-percent-tissue-culture-infective-dose ($TCID_{50}$) per mL (($TCID_{50}$)/mL).

The sample was also used to determine the presence or absence of a hook effect (also known as a high-dose hook effect). A hook effect is caused by an excess of the target protein, which reacts concomitantly and instantaneously with both the immobilized and labeled antibodies. Thus, the hook effect refers to the false negative result which can be seen when very high levels of target are present in a tested sample. To overcome a hook effect, dilution of specimens may be necessary. As shown in (FIG. 1), no hook effect was apparent at concentrations up to and including $1.0 \times 10^{5.8}$ (630,957) ($TCID_{50}$)/mL.

Example 6

Clinical Evaluation of Nasopharyngeal and Nasal Specimens with the Lateral Flow Devices Exemplary lateral flow devices were used for clinical evaluation of sensitivity and specificity against a reference method comprising RealTime PCR (RT-PCR) of SARS-CoV-2 in samples from nasopharyngeal specimens of patients suspected of COVID-19 infection. The exemplary lateral flow device comprised full-length versions of the first and second antibodies described herein.

The exemplary lateral flow device comprising full-length antibodies was found to have a sensitivity (also referred to as percent positive agreement above) of approximately 91% for all samples, when compared to RT-PCR analysis (Table 6). The specificity (also referred to as percent negative agreement above) was over 99%.

The samples were also classified based on days post symptom onset. As shown in Table 7, the sensitivity was greater than 90% for all positive subjects 0-7 days post symptom onset. In addition, the specificity was 100% for negative subjects 0-3 days post symptom onset and greater than 99% for negative subjects 4-7 days post symptom onset.

TABLE 6

| | | Nasopharyngeal RT-PCR Test | | |
| --- | --- | --- | --- | --- |
| | | Positive | Negative | Total |
| Lateral Flow | Positive | 128 | 1 | 129 |
| | Negative | 12 | 444 | 456 |
| | Total | 140 | 445 | 585 |
| Sensitivity (95% CI) | | 91.4% (85.5%-95.5%) | | |
| Specificity (95% CI) | | 99.8% (98.8%-100.0%) | | |
| Total Agreement (95% CI) | | 97.8% (96.2%-98.8%) | | |

TABLE 7

| Days Post Symptom Onset | N | # Positive Subjects | # True Positive Subjects | Sensitivity (95% CI) | # Positive Subject | # True Positive Subjects | Specificity (95% CI) | Total Agreement (95% CI) |
|---|---|---|---|---|---|---|---|---|
| 0-3 | 172 | 39 | 37 | 94.9% (82.7%-99.4%) | 133 | 133 | 100% (97.3%-100%) | 98.8% (95.9%-99.9%) |
| 4-7 | 404 | 101 | 91 | 90.1% (82.5%-95.1%) | 303 | 302 | 99.7% (98.2%-100%) | 97.3% (95.2%-98.6%) |
| No symptoms | 9 | 0 | 0 | N/A | 9 | 9 | 100% (66.4%-100%) | 100% (66.4%-100%) |

Exemplary lateral flow devices were used for testing clinical sensitivity and specificity against a reference method comprising RealTime PCR (RT-PCR) of SARS-CoV-2 in samples from nasal swabs of patients suspected of COVID-19 infection. The exemplary lateral flow device comprised full-length versions of the first and second antibodies described herein.

The exemplary lateral flow device comprising full-length antibodies was found to have a sensitivity of approximately 91% for all samples, when compared to RT-PCR analysis (Table 8). The specificity was greater than 99%.

The samples were also classified based on days post symptom onset. As shown in Table 9, The sensitivity was greater than 90% for all positive subjects 0-7 days post symptom onset. In addition, the specificity was 100% for negative subjects 4-7 days post symptom onset and greater than 99% for negative subjects 4-7 days post symptom onset.

In addition, the RT-PCR was completed using the remaining sample after a portion or the majority of the sample was used in the later flow assay, rather than a second sample, as described in Example 4 and used above.

The exemplary lateral flow device comprising full-length antibodies was found to have a sensitivity of approximately 98% for all samples, when compared to RT-PCR analysis of the remaining sample (Table 10). The specificity was greater than 99%. With a total agreement over 99%.

The samples were also group by days post symptom onset. As shown in Table 11, The sensitivity was 100% for all positive subjects 0-3 days post symptom onset and greater than 96% for all positive subjects 4-7 days post symptom onset. In addition, the specificity was 100% for negative subjects 4-7 days post symptom onset and greater than 99% for negative subjects 4-7 days post symptom onset.

TABLE 8

| | | Nasopharyngeal RT-PCR Test | | |
|---|---|---|---|---|
| | | Positive | Negative | Total |
| Lateral Flow | Positive | 102 | 1 | 103 |
| | Negative | 10 | 397 | 407 |
| | Total | 112 | 398 | 510 |
| Sensitivity (95% CI) | | 91.1% (84.2%-95.6%) | | |
| Specificity (95% CI) | | 99.7% (98.6%-100.0%) | | |
| Total Agreement (95% CI) | | 97.8% (96.2%-98.9%) | | |

TABLE 10

| | | Nasopharyngeal RT-PCR Test | | |
|---|---|---|---|---|
| | | Positive | Negative | Total |
| Lateral Flow | Positive | 102 | 1 | 103 |
| | Negative | 2 | 403 | 405 |
| | Total | 104 | 404 | 508 |
| Sensitivity (95% CI) | | 98.1% (93.2%-99.8%) | | |
| Specificity (95% CI) | | 99.8% (98.6%-100.0%) | | |
| Total Agreement (95% CI) | | 99.4% (98.3%-99.9%) | | |

TABLE 9

| Days Post Symptom Onset | N | # Positive Subjects | # True Positive Subjects | Sensitivity (95% CI) | # Positive Subject | # True Positive Subjects | Specificity (95% CI) | Total Agreement (95% CI) |
|---|---|---|---|---|---|---|---|---|
| 0-3 | 227 | 50 | 46 | 92.0% (80.8%-97.8%) | 177 | 176 | 99.4% (96.9%-100%) | 97.8% (94.9%-99.3%) |
| 4-7 | 272 | 62 | 56 | 90.3% (80.1%-96.4%) | 210 | 210 | 100% (98.3%-100%) | 97.8% (95.3%-99.2%) |
| No symptoms | 11 | 0 | 0 | N/A | 11 | 11 | 100% (71.5%-100%) | 100% (71.5%-100%) |

TABLE 11

| Days Post Symptom Onset | N | # Positive Subjects | # True Positive Subjects | Sensitivity (95% CI) | # Positive Subject | # True Positive Subjects | Specificity (95% CI) | Total Agreement (95% CI) |
| --- | --- | --- | --- | --- | --- | --- | --- | --- |
| 0-3 | 226 | 46 | 46 | 100.0% (92.3%-100%) | 180 | 179 | 99.4% (96.9%-100%) | 99.6% (97.6%-100%) |
| 4-7 | 271 | 58 | 56 | 96.6% (88.1%-99.6%) | 213 | 213 | 100% (98.3%-100%) | 99.3% (97.4%-99.9%) |
| No symptoms | 11 | 0 | 0 | N/A | 11 | 11 | 100% (71.5%-100%) | 100% (71.5%-100%) |

Example 7

SARS-CoV-2 Variants

To evaluate the impact of nucleocapsid mutations found in circulating SARS-CoV-2 strains, including delta and lambda strains, recombinant proteins were prepared that carry mutations identified in clinical specimens for testing. Mutations tested individually or in combinations included: D63G, R203K, R203M, G204R, R209I, A220V, Q229H, M234I, S235F, D348Y, P365S, E367Q, A376T, D377Y and a wildtype (WT) Wuhan reference control. These mutations represent the unique nucleocapsid sequence profiles of several circulating lineages: B.1.1.7, B.1.617.1, B.1.617.2, B.1.617.3, B.1.618, AY.1, AY.2, P.2, B.1.526, B.1.526.1, B.1.526.2, and a panel of strains from Italy. Western blots and high-throughput immunoassays conducted with antibodies as disclosed herein confirmed detection of all mutant and WT recombinant antigens (rAg) at a sensitivity equivalent to the WT control.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art and may be made without departing from the spirit and scope thereof.

What is claimed is:

1. A method of detecting SARS-CoV-2 virus in a sample obtained from a subject, wherein the method is an immunoassay, comprising:
   contacting a sample obtained from a subject with a first antibody or antigen-binding fragment thereof which specifically binds to the nucleocapsid (N) protein from the SARS-CoV-2 virus, or a fragment thereof, under conditions which allow binding of the N protein from the SARS-CoV-2 virus, or a fragment thereof, if present in the sample, to the first antibody or antigen-binding fragment thereof, wherein the first antibody or antigen-binding fragment thereof comprises:
   (i) a heavy chain variable region comprising a complementarity determining region 1 (CDR) amino acid sequence of SEQ ID NO: 1, a CDR2 amino acid sequence of SEQ ID NO: 2, and a CDR3 amino acid sequence of SEQ ID NO: 3,
   (ii) a light chain variable region comprising a CDR1 amino acid sequence of SEQ ID NO: 4, a CDR2 amino acid sequence of SEQ ID NO: 5, and a CDR3 amino acid sequence of SEQ ID NO: 6;
   contacting the sample with a conjugate comprising a second antibody which specifically binds to N protein from the SARS-CoV-2 virus, or a fragment thereof, and a detectable label wherein the second antibody or antigen-binding fragment thereof binds to a different epitope than the first antibody, or antigen-binding fragment thereof, and comprises:
   (i) a heavy chain variable region comprising a complementarity determining region 1 (CDR) amino acid sequence of SEQ ID NO: 9, a CDR2 amino acid sequence of SEQ ID NO: 10, and a CDR3 amino acid sequence of SEQ ID NO: 11,
   (ii) a light chain variable region comprising a CDR1 amino acid sequence of SEQ ID NO: 12, a CDR2 amino acid sequence of SEQ ID NO: 13, and a CDR3 amino acid sequence of SEQ ID NO: 14; and
   assessing the presence of a signal from the detectable label, wherein the presence of a signal from the detectable label indicates the presence of the N protein from the SARS-CoV-2 virus, or a fragment thereof in the sample.

2. The method of claim 1, wherein the immunoassay is an enzyme-linked immunosorbent assay (ELISA) or a lateral flow immunoassay (LFA).

3. The method of claim 1, wherein the sample comprises saliva, mucus, blood, serum, or plasma.

4. The method of claim 1, wherein the first antibody, or antigen-binding fragment thereof, comprises a heavy chain variable region amino acid sequence of SEQ ID NO: 7 and a light chain variable region amino acid sequence of SEQ ID NO: 8.

5. The method of claim 1, wherein the second antibody, or antigen-binding fragment thereof, comprises a heavy chain variable region amino acid sequence of SEQ ID NO: 15 and a light chain variable region amino acid sequence of SEQ ID NO: 16.

6. The method of claim 1, further comprising detection of at least one or more additional pathogens, or antigens thereof.

7. A lateral flow device comprising:
   a first antibody, or antigen-binding fragment thereof, which specifically binds to the nucleocapsid (N) protein from the SARS-CoV-2 virus, or a fragment thereof, wherein the first antibody or antigen-binding fragment thereof binds to a different epitope than the first antibody or antigen-binding fragment thereof, and comprises:
   (i) a heavy chain variable region comprising a complementarity determining region 1 (CDR) amino acid sequence of SEQ ID NO: 1, a CDR2 amino acid sequence of SEQ ID NO: 2, and a CDR3 amino acid sequence of SEQ ID NO: 3,
   (ii) a light chain variable region comprising a CDR1 amino acid sequence of SEQ ID NO: 4, a CDR2 amino acid sequence of SEQ ID NO: 5, and a CDR3 amino acid sequence of SEQ ID NO: 6; and
   a second antibody, or antigen-binding fragment thereof, which specifically binds to a protein from the SARS-CoV-2 virus, or a fragment thereof, wherein the second antibody or antigen-binding fragment thereof comprises:
   (i) a heavy chain variable region comprising a complementarity determining region 1 (CDR) amino acid sequence of SEQ ID NO: 9, a CDR2 amino acid sequence of SEQ ID NO: 10, and a CDR3 amino acid sequence of SEQ ID NO: 11,
   (ii) a light chain variable region comprising a CDR1 amino acid sequence of SEQ ID NO: 12, a CDR2 amino acid sequence of SEQ ID NO: 13, and a CDR3 amino acid sequence of SEQ ID NO: 14.

8. The lateral flow device of claim 7, wherein the first antibody, or antigen-binding fragment thereof, is immobilized.

9. The lateral flow device of claim 7, wherein the second antibody, or antigen-binding fragment thereof, comprises a detectable label.

10. The lateral flow device of claim 7, wherein the lateral flow device comprises a sample pad and the second antibody, or antigen-binding fragment thereof is included on the sample pad.

11. The lateral flow device of claim 7, wherein the lateral flow device comprises a test line comprising the first antibody, or antigen-binding fragment thereof.

12. A kit comprising the lateral flow device of claim 7 in a sealed package.

13. The kit of claim 12, further comprising an extraction buffer.

14. The kit of claim 12, further comprising a sampling device.

15. The kit of claim 14, wherein the sampling device comprises a nasal swab.

* * * * *